(12) United States Patent
Shaban et al.

(10) Patent No.: US 10,471,289 B2
(45) Date of Patent: Nov. 12, 2019

(54) CARBON-MODIFIED TITANIUM DIOXIDE NANOPARTICLES AND THE PHOTOCATALYTIC REMEDIATION OF AQUEOUS SOURCES SYSTEMS AND METHODS THEREOF

(71) Applicant: King Abdulaziz University, Jeddah (SA)

(72) Inventors: Yasser A. Shaban, Jeddah (SA); Mohamed A. El Sayed, Alexandria (EG); Amr A. El Maradny, Jeddah (SA); Radwan Kh. Al Farawati, Jeddah (SA); Mosa I. Al Zobidi, Jeddah (SA); Shahed U. M. Khan, Pittsburgh, PA (US)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/729,904

(22) Filed: Oct. 11, 2017

(65) Prior Publication Data

US 2018/0185688 A1 Jul. 5, 2018

Related U.S. Application Data

(60) Provisional application No. 62/442,204, filed on Jan. 4, 2017.

(51) Int. Cl.
*A62D 3/34* (2007.01)
*B01J 35/00* (2006.01)
(Continued)

(52) U.S. Cl.
CPC .............. *A62D 3/34* (2013.01); *B01J 21/063* (2013.01); *B01J 21/18* (2013.01); *B01J 27/20* (2013.01);
(Continued)

(58) Field of Classification Search
CPC ......... A62D 3/176; A62D 3/32; B01J 21/063; B01J 35/004; C01G 23/047;
(Continued)

(56) References Cited

U.S. PATENT DOCUMENTS 9,334,183 B2 5/2016 Fahs, II et al.
2004/0073078 A1 4/2004 Osada et al.
(Continued)

FOREIGN PATENT DOCUMENTS

DE 196 02 947.3 7/1997
JP 4018161 12/2007
WO 89/00985 2/1989

OTHER PUBLICATIONS

Barborini et al. "Nanostructured TiO2Films with 2 eVOptical Gaps", Adv.Mater.2005,17, 1842-1846 (Year: 2005).*
(Continued)

*Primary Examiner* — Amber R Orlando
*Assistant Examiner* — Syed T Iqbal
(74) *Attorney, Agent, or Firm* — Oblon, McClelland, Maier & Neustadt, L.L.P.

(57) ABSTRACT

A closed-loop system and methods for the remediation of an aqueous solution comprising a polychlorinated biphenyl employing carbon modified titanium dioxide nanoparticles having a Ti:C atomic ratio of 3:1 to 6:1 and a bandgap energy of 1.4-2.0 eV as photocatalysts.

18 Claims, 24 Drawing Sheets

(51) Int. Cl.

| | | |
|---|---|---|
| *C07C 25/18* | (2006.01) | |
| *B01J 21/06* | (2006.01) | |
| *C01G 23/053* | (2006.01) | |
| *B01J 37/03* | (2006.01) | |
| *B01J 37/08* | (2006.01) | |
| *B01J 21/18* | (2006.01) | |
| *B01J 27/20* | (2006.01) | |
| *C02F 1/72* | (2006.01) | |
| *C01G 23/047* | (2006.01) | |
| *A62D 101/28* | (2007.01) | |
| *C02F 101/32* | (2006.01) | |

(52) U.S. Cl.
CPC ......... *B01J 35/004* (2013.01); *B01J 35/0013* (2013.01); *B01J 37/033* (2013.01); *B01J 37/036* (2013.01); *B01J 37/086* (2013.01); *C01G 23/053* (2013.01); *C02F 1/725* (2013.01); *C07C 25/18* (2013.01); *A62D 2101/28* (2013.01); *B01J 35/002* (2013.01); *C01G 23/047* (2013.01); *C01P 2002/30* (2013.01); *C01P 2002/60* (2013.01); *C01P 2002/72* (2013.01); *C01P 2002/76* (2013.01); *C01P 2002/77* (2013.01); *C01P 2002/84* (2013.01); *C01P 2004/03* (2013.01); *C01P 2004/64* (2013.01); *C02F 2101/327* (2013.01); *C02F 2305/08* (2013.01); *C02F 2305/10* (2013.01)

(58) Field of Classification Search
CPC ............... C01G 23/053; C01P 2002/30; C01P 2002/60; C01P 2002/72; C01P 2002/76; C01P 2002/77; C01P 2002/84; C01P 2004/03; C01P 2004/64; C07C 25/18
See application file for complete search history.

(56) References Cited

U.S. PATENT DOCUMENTS

2006/0210798 A1  9/2006  Burda
2017/0130181 A1* 5/2017  Emminger ............ C12M 21/02

OTHER PUBLICATIONS

Suhasini Desai et al., "TiO2 Assisted Photocatalysts: A Novel Method for Water Treatment," Journal of Indian Water Works Association, Apr.-Jun. 2012, pp. 149-157.

G. Impellizzeri et al., "C Ion-Implanted TiO2 Thin Film for Photocatalytic Applications," Journal of Applied Physics, vol. 117, No. 10, Mar. 2015, 8 Pages.

Antoni W Morawski et al., "Carbon Modified TiO2 Photocatalysts for Water Purification," Polish Journal of Chemical Technology, vol. 11, No. 2, Jun. 2009, pp. 46-50.

Yasser A. Shaban et al., "Photocatalytic Removal of Polychlorinated Biphenyls (PCBs) Using Carbon Modified Titanium Oxide Nanoparticles," Applied Surface Science, vol. 365, 2016, pp. 108-113.

* cited by examiner

CARBON-MODIFIED TITANIUM DIOXIDE NANOPARTICLES AND THE PHOTOCATALYTIC REMEDIATION OF AQUEOUS SOURCES SYSTEMS AND METHODS THEREOF

CROSS REFERENCE TO RELATED APPLICATIONS

This application claims the benefit of priority from U.S. Provisional Application No. 62/442,204 filed Jan. 4, 2017, the entire contents of which are herein incorporated by reference.

BACKGROUND OF THE DISCLOSURE

Technical Field

The present disclosure relates to a closed-loop system and methods for the remediation of an aqueous solution comprising a polychlorinated biphenyl employing a photocatalyst comprising carbon modified titanium dioxide nanoparticles

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Polychlorinated biphenyls (PCBs) are toxic xenobiotics which were widely used in industry as hydraulic fluids, heat transfer fluids, capacitors, solvent extenders, plasticizers, and dielectric fluids [D. A. Abramowicz, M. J. Brennan, H. M. Van Dort, E. L. Gallagher, Environ. Sci. Technol. 27 (1993) 1125-1131.]. PCBs are mixtures of up to 209 individual chlorinated compounds containing different numbers of chlorine atoms per molecule known as congeners. PCB mixtures are commercially known as Aroclor. The Aroclors are identified by a four-digit-numbering code in which the first two digits "12" indicate that the product is derived from biphenyl, and the last two digits indicate the approximate chlorine content by weight percent. Thus, Aroclor 1254 and Aroclor 1260 contain about 54% and 69% chlorine, respectively [C. H. Walker, Organic Pollutants: An Ecotoxicological Perspective, Taylor &Francis, Inc., 2002.]. Aroclor 1254 and 1260 were found to be the most commonly used PCBs commercial mixtures. Because of their bioaccumulation and resistance to biodegradation, the discharge of these pollutants into water supplies causes a serious threat to the environment as well as public health.

Polychlorinated biphenyls (PCBs) are a class of persistent organic pollutants that are ubiquitous in the environment. The U.S. EPA has classified PCBs as compounds with significant human health risk, due to their toxicity, carcinogenicity, and bioaccumulation nature [United States Environmental Protection Agency, "National air toxics information report: qualitative and quantitative carcinogenic risk assessment," EPA 450/5-87-003, US Environmental Protection Agency and STAPPA/ALAPCO, Washington, D.C., USA, 1987.]. Therefore, the release of these pollutants into water resources poses a serious threat to human health and the environment [E. H. Buckley, "Accumulation of airborne polychlorinated biphenyls in foliage," Science, vol. 216, no. 4545, pp. 520-522, 1982.]. Though their production has been prohibited, they are still remaining in large quantities in industrial fluids, heat exchangers, and plasticizers. Though their production was banned, PCBs are still being detected in environmental matrixes, including air, seawater, and sediment.

Conventional treatment technology for PCBs including incineration, biodegradation, microwave irradiation, sub and supercritical water treatment are lengthy or expensive [G. Anitescu, L. L. Tavlarides, Ind. Eng. Chem. Res. 39 (2000) 583-591; and X. Liu, G. Yu, Chemosphere 63 (2006) 228-235; and N. Yamasaki, T. Yasui, K. Matsuoka, Environ. Sci. Technol. 14 (1980) 550-552.]. Incineration is the main remediation technology for PCBs. However, it demands expensive facilities and high temperatures of more than 1200° C. [M. L. Hitchman, R. A. Spackman, N. C. Ross, and C. Agra, "Disposal methods for chlorinated aromatic waste," Chemical Society Reviews, vol. 24, no. 6, pp. 423-430, 1995.]. Recently, heterogeneous photocatalytic technology involving $TiO_2$ based semiconductors under light irradiation has shown potential advantages to be used as an alternative remedial technology, because it is inexpensive and can rapidly and completely mineralize organic pollutants. $TiO_2$ has been studied extensively for practical utilization for water splitting, remedy of many organic pollutants, and treatment of wastewater [S. U. M. Khan, M. Al-Shahry, and W. B. Ingler Jr., "Efficient photochemical water splitting by a chemically modified n-$TiO_2$," Science, vol. 297, no. 5590, pp. 2243-2245, 2002; and Y. A. Shaban and S. U. M. Khan, "Photoresponse of visible light active CM-n-$TiO_2$, HM-n-$TiO_2$, CM-n-$Fe_2O_3$, and CM-p-$WO_3$ towards water splitting reaction," International Journal of Photoenergy, vol. 2012, Article ID 749135, 20 pages, 2012; and Y. A. Shaban, M. A. El Sayed, A. A. El Maradny, R. K. Al Farawati, and M. I. Al Zobidi, "Photocatalytic degradation of phenol in natural seawater using visible light active carbon modified (CM)-n-$TiO_2$ nanoparticles under UV light and natural sunlight illuminations," Chemosphere, vol. 91, no. 3, pp. 307-313, 2013; and H. Park and W. Choi, "Photocatalytic reactivities of nafioncoated $TiO_2$ for the degradation of charged organic compounds under UV or visible light," Journal of Physical Chemistry B, vol. 109, no. 23, pp. 11667-11674, 2005; and C. Xu, R. Killmeyer, M. L. Gray, and S. U. M. Khan, "Photocatalytic effect of carbon-modified n-TiO2 nanoparticles under visible light illumination," Applied Catalysis B: Environmental, vol. 64, no, 3-4, pp. 312-317, 2006; and Y. A. Shaban, M. A. El Sayed, A. A. El Maradny, R. K. Al Farawati, M. I. Al Zobidi, and S. U. M. Khan, "Photocatalytic removal of polychlorinated biphenyls (PCBs) using carbonmodified titaniumoxide nanoparticles," Applied Surface Science, vol. 365, pp. 108-113, 2016; and K. Yamaguti and S. J. Sato, "Photolysis of water overmetallized powdered titanium dioxide," Journal of the Chemical Society, Faraday Transactions 1: Physical Chemistry in Condensed Phases, vol. 81, no. 5, pp. 1237-1246, 1985; and T. Oppenlander, Photochemical Purification of Water and Air, Wiley-VCH, Weinheim, Germany, 2003; and S. Parsons," Advanced Oxidation Processes for Water and Wastewater Treatment, IWA Publishing, Cornwall, UK, 2004.—each incorporated herein by reference in its entirety]. However, $TiO_2$ photocatalysis is limited to UV light, as a result of its wide bandgap (3.0-3.2 eV). To overcome this drawback, several studies have been performed to modify $TiO_2$ with nitrogen, sulfur, and transition metals to extend its photoresponse to the visible region by narrowing its bandgap energy [C. Burda, Y. Lou, X. Chen, A. C. S. Samia, J. Stout, and J. L. Gole, "Enhanced nitrogen doping in $TiO_2$ nanoparticles," *NanoLetters*, vol. 3, no. 8, pp. 1049-1051, 2003; and R. Asahi, T. Morikawa, T. Ohwaki, K. Aoki, and Y. Taga, "Visible-light photocatalysis in nitrogen-doped titanium oxides," *Science*, vol. 293, no. 5528, pp. 269-271, 2001; and T. Umebayashi, T. Yamaki, H. Itoh, and K. Asai, "Band gap narrowing of titanium dioxide by sulfur doping," *Applied Physics Letters,"* vol. 81, no. 3, pp. 454-456, 2002; and W. Choi, A. Termin, and M. R. Hoffmann, "The role of metal ion dopants in quantum-sized TiO2: correlation between photoreactivity and charge carrier recombination dynamics," *Journal of Physical Chemistry*, vol. 98, no. 51, pp. 13669-13679, 1994; and M. Anpo, "Photocatalysis on titanium oxide catalysts—approaches in achieving highly efficient reactions and realizing the use of visible light," *Catalysis Surveys from Japan*, vol. 1, no. 2, pp. 169-179, 1997.— each incorporated herein by reference in its entirety]. Recently, it has been evidently demonstrated that modification of $TiO_2$ by carbon enhanced its photoresponse by narrowing its bandgap energy.

In view of the forgoing, one aspect of the present disclosure is to provide a pilot-plant scale or larger closed-loop system for the photocatalytic remediation of a polychlorinated biphenyl contaminated aqueous solution, preferably seawater, under irradiation, preferably by natural solar light. A further aim of the present disclosure is to provide carbon modified titanium dioxide nanoparticles as photocatalysts for use in the system, as well as, methods employing the system and the photocatalysts.

BRIEF SUMMARY OF THE DISCLOSURE

According to a first aspect, the present disclosure relates to a closed-loop system for the remediation of an aqueous solution comprising a polychlorinated biphenyl, the system comprising i) a vessel comprising an aqueous solution comprising a first amount of at least one polychlorinated biphenyl and carbon modified titanium dioxide nanoparticles having a Ti:C atomic ratio in the range of 3:1 to 6:1 and a bandgap in the range of 1.4-2.0 eV dispersed in the aqueous solution, ii) a pump, optionally iii) a light source having a wavelength in the ultraviolet or visible region, iv) a tray oriented at a tilt angle from the horizontal comprising a distributor end and an opposing collector end located at a lower vertical height than the distributor end, and optionally v) a mixer configured to agitate the aqueous solution in the vessel, wherein the vessel is configured to deliver the aqueous solution through the pump to the distributor end of the tray, wherein the tray is configured to flow the aqueous solution from the distributor end to the collector end while exposing the aqueous solution to a light source forming a remediated aqueous solution comprising a second amount of the at least one polychlorinated biphenyl, wherein the collector end is configured to return the remediated aqueous solution to the vessel, and wherein the first amount of the at least one polychlorinated biphenyl is greater than the second amount of the at least one polychlorinated biphenyl.

In one embodiment, the carbon modified titanium dioxide nanoparticles have a 5-15% atomic percentage of carbon relative to the total atomic percentage of the carbon modified titanium dioxide nanoparticles.

In one embodiment, the carbon modified titanium dioxide nanoparticles have an average crystal size of 25-35 nm.

In one embodiment, the tray is oriented at a tilt angle of 5-40° from the horizontal.

In one embodiment, the aqueous solution is seawater which has a salinity of 10-100 g/L and a pH in the range of 4-7 and the light source is the sun.

In one embodiment, the carbon modified titanium dioxide nanoparticles are present in an amount in the range of 0.1-1.5 g of carbon modified titanium dioxide nanoparticles per 1.0 L of the aqueous solution.

According to a second aspect, the present disclosure relates to a method for remediating an aqueous solution comprising at least one polychlorinated biphenyl employing the system of the present disclosure in any of its embodiments, the method comprising i) flowing the aqueous solution from the vessel through the pump to the distributor end of the tray, ii) flowing the aqueous solution from the distributor end of the tray to the collector end of the tray via gravity while exposing the aqueous solution to the light source thereby photocatalytically degrading or mineralizing the at least one polychlorinated biphenyl to obtain the remediated aqueous solution, and iii) returning the remediated aqueous solution to the vessel.

In one embodiment, greater than 70% by weight of the polychlorinated biphenyl relative to the first amount of the at least one polychlorinated biphenyl is photocatalytically degraded or mineralized after the exposing is carried out for a time period of 10-60 minutes.

In one embodiment, the aqueous solution, the remediated aqueous solution, or both continuously circulates in a closed-loop circuit.

In one embodiment, at least 50% by weight of the polychlorinated biphenyl relative to the first amount of the at least one polychlorinated biphenyl is photocatalytically degraded or mineralized after the exposing is carried out for a time period of less than 20 minutes and this time period is 40-60% less than a time period wherein at least 50% by weight of the polychlorinated biphenyl relative to the first amount of the polychlorinated biphenyl is photocatalytically degraded or mineralized by exposure in a substantially similar method employing a substantially similar system in a substantially similar manner with titanium dioxide nanoparticles which have a Ti:C atomic ratio of greater than 50:1.

In one embodiment, greater than 90% by weight of the polychlorinated biphenyl relative to the first amount of the at least one polychlorinated biphenyl is photocatalytically degraded or mineralized after the exposing is carried out for a time period of less than 60 minutes.

According to a third aspect, the present disclosure relates to a photocatalyst comprising carbon modified titanium dioxide nanoparticles which have a Ti:C atomic ratio in the range of 3:1 to 6:1, wherein the photocatalyst has a bandgap in the range of 1.4-2.0 eV.

In one embodiment, the photocatalyst has a 5-15% atomic percentage of carbon relative to the total atomic percentage of the photocatalyst.

In one embodiment, carbon modified titanium dioxide nanoparticles have an average crystal size of 25-35 nm.

According to a fourth aspect, the present disclosure relates to a method for remediating an aqueous solution comprising at least one polychlorinated biphenyl, the method comprising i) contacting the photocatalyst of the present disclosure in any of its embodiments with the aqueous solution comprising at least one polychlorinated biphenyl to form a treated aqueous solution and ii) exposing the treated aqueous solution to a light source having a wavelength in the ultraviolet or visible region thereby photocatalytically degrading or mineralizing the at least one polychlorinated biphenyl to form a remediated aqueous solution.

In one embodiment, the aqueous solution is seawater having a salinity of 10-100 g/L and a pH in the range of 4-7 and the light source is the sun.

In one embodiment, the photocatalyst is present in an amount in the range of 0.1-1.5 g of photocatalyst per 1.0 L of aqueous solution.

In one embodiment, the polychlorinated biphenyl is present in the aqueous solution in an amount in the range of 0.1-1.5 ppm.

In one embodiment, a removal efficiency of the polychlorinated biphenyl is at least 2 times greater than a removal efficiency of a substantially similar method performed in a substantially similar manner with a photocatalyst which has a Ti:C atomic ratio of greater than 50:1.

In one embodiment, greater than 70% by weight of the polychlorinated biphenyl is photocatalytically degraded or mineralized after the exposing is carried out for a time period of 1-25 minutes.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
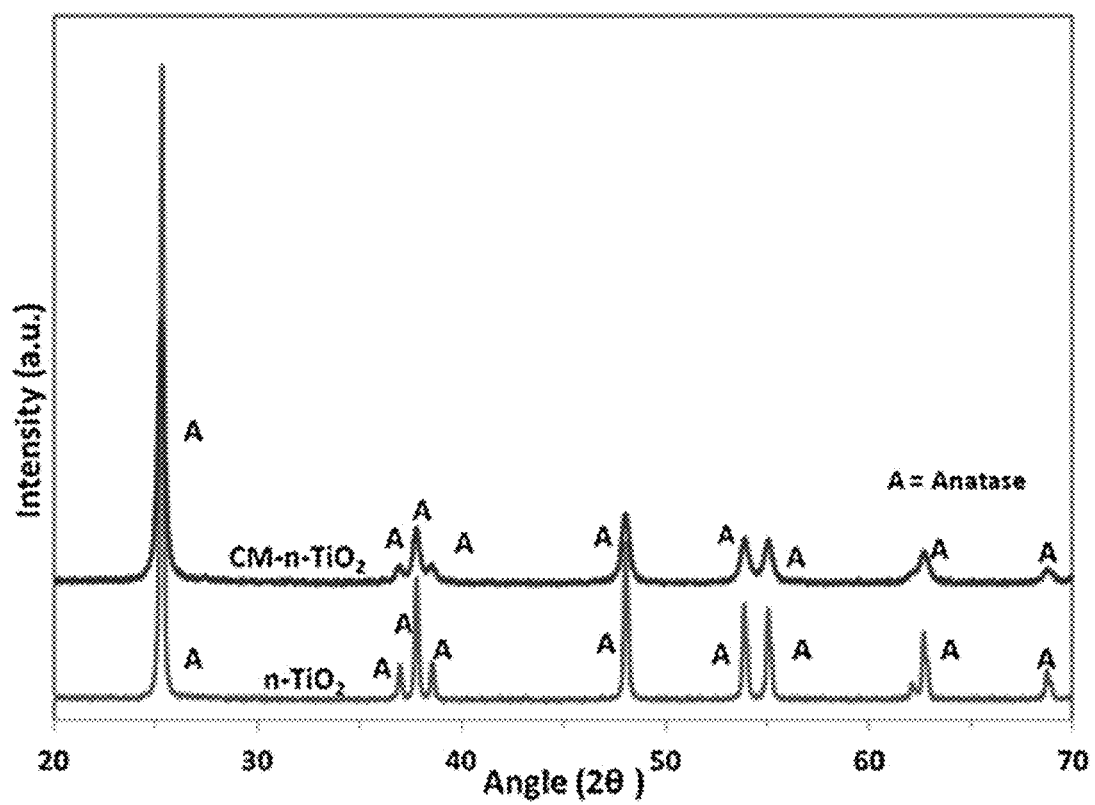
FIG. 1 is an X-ray diffraction (XRD) pattern of an unmodified titanium dioxide nanoparticle (n-$TiO_2$) photocatalyst and a carbon-modified titanium dioxide nanoparticle (CM-n-$TiO_2$) photocatalyst.

Embodiments of the present disclosure will now be described more fully hereinafter with reference to the accompanying drawings, in which some, but not all of the embodiments of the disclosure are shown.

As used herein, the words "a" and "an" and the like carry the meaning of "one or more". Additionally, within the description of this disclosure, where a numerical limit or range is stated, the endpoints are included unless stated otherwise. Also, all values and subranges within a numerical limit or range are specifically included as if explicitly written out.

According to a first aspect, the present disclosure relates to a closed-loop system for the remediation of an aqueous solution comprising a polychlorinated biphenyl, the system comprising i) a vessel comprising an aqueous solution comprising a first amount of at least one polychlorinated biphenyl and carbon modified titanium dioxide nanoparticles having a Ti:C atomic ratio in the range of 3:1 to 6:1 and a bandgap in the range of 1.4-2.0 eV dispersed in the aqueous solution, ii) a pump, optionally iii) a light source having a wavelength in the ultraviolet or visible region, iv) a tray oriented at a tilt angle from the horizontal comprising a distributor end and an opposing collector end located at a lower vertical height than the distributor end, and optionally v) a mixer configured to agitate the aqueous solution in the vessel, wherein the vessel is configured to deliver the aqueous solution through the pump to the distributor end of the tray, wherein the tray is configured to flow the aqueous solution from the distributor end to the collector end while exposing the aqueous solution to the light source forming a remediated aqueous solution comprising a second amount of at least one polychlorinated biphenyl, wherein the collector end is configured to return the remediated aqueous solution to the vessel, and wherein the first amount of the at least one polychlorinated biphenyl is greater than the second amount of at least one polychlorinated biphenyl.

According to another aspect, the present disclosure relates to a photocatalyst comprising carbon modified titanium dioxide nanoparticles which have a Ti:C atomic ratio in the range of 3:1 to 6:1, wherein the photocatalyst has a bandgap in the range of 1.4-2.0 eV.

The system components may be directly connected or fluidly connected to one another, for example by connecting pipes without intervening components. In addition, valves may be disposed in a variety of ways, for example between portions of connecting pipes, or for example, integrally to any additional or other system components. Depending on the size of the closed-loop system described herein the internal diameters of 1-1000 mm, preferably 2-500 mm, preferably 5-100 mm, preferably 10-60 mm, preferably 15-50 mm, preferably 20-40 mm, although the internal diameters of the connecting pipes and valves may be variable.

In one aspect of the system a vessel comprising an aqueous solution comprising a first amount of at least one polychlorinated biphenyl and carbon modified titanium dioxide nanoparticles having a Ti:C atomic ratio in the range of 3:1 to 6:1 and a bandgap in the range 1.4-2.0 eV dispersed in the aqueous solution is present and is configured to deliver the aqueous solution through the pump to the distributor end of the tray. Further, the collector end of the tray is configured to return the remediated aqueous solution to the vessel.

As used herein, a "vessel", "tank", "batch tank" or "batch reactor" are used interchangeably and refer to a generic term for a type of vessel widely used in the process industries. The batch tank may refer to a vessel of this type typically used in a variety of processes including operations such as solids dissolution, product mixing, chemical reactions, batch distillation, crystallization, liquid/liquid extraction and polymerization. In a preferred embodiment, the batch tank comprises a tank with an agitator and optionally an integral heating/cooling system. The batch tank may be constructed of a material, such as metal, plastic, ceramic or glass that can withstand the temperatures and pressures associated with the operation of the system. In a preferred embodiment, the batch tank is fabricated in at least one selected from the group consisting of steel, stainless steel, glass-lined steel, glass or exotic alloy. In a preferred embodiment, the batch tank has a volume of 1-15000 L, preferably 5-10000 L, preferably 10-5000 L, preferably 20-1000 L, preferably 25-500 L, preferably 30-100 L. In certain embodiments, the batch tank may comprise a heating and/or cooling system to hold the batch tank contents at a desired temperature. This may consist of a way to add or remove heat by means of a cooling jacket or cooling pipe. Exemplary suitable heating and/or cooling systems include, but are not limited to, a single external jacket, a half coil jacket, a constant flux cooling jacket, and the like. In certain embodiments, the batch tank may further comprise means of charging liquids and solids, preferably via connection in the top cover of the batch tank as well as means of discharging vapors and gases through connections and discharging liquids through the bottom of the batch tank.

In one aspect, the system comprises a mixer or agitator configured to agitate the aqueous solution in the batch tank. The aqueous solution may be shaken/stirred throughout the duration of the operation of the system by employing a rotary shaker, a magnetic stirrer, or an overhead stirrer. In a preferred embodiment, the agitator or mixer arrangement is a centrally mounted driveshaft with an overhead drive unit. Impeller blades may be mounted on the shaft. A wide variety of blade designs may be used and typically the blades cover about two thirds of the diameter of the reactor or batch tank, preferably at least half of the diameter of the reactor or batch tank. In certain embodiments, anchor shaped paddles may be used often having a close clearance between the blade and the vessel walls. In certain embodiments, the batch tank or reactor may further comprise baffles. These stationary blades may break up flow caused by the rotating agitator or mixer. These baffles may be fixed to the vessel cover or mounted on the interior of the side walls. In certain embodiments, higher mixing rates may be achieved by using smaller flowing systems with high speed agitators, such as, for example, ultrasonic mixing or static mixers. In certain embodiments, the aqueous solution may be left to stand (i.e. not stirred). In certain embodiments, the aqueous solution may be sonicated.

As used herein a polychlorinated biphenyl (PCB) is an organic chlorine compound with the formula $C_{12}H_{10-x}Cl_x$, wherein x is a whole number. Polychlorinated biphenyls were once widely deployed as dielectric and coolant fluids in electrical apparatus, carbonless copy paper and in heat transfer fluids. PCBs have demonstrated environmental toxicity and been classified as a persistent, organic pollutant as well as causing cancer in animals and being termed a probable or definite carcinogen in humans. Some PCBs share a structural similarity and toxic mode of action with dioxin.

The polychlorinated biphenyls are typically pale yellow viscous liquids. They are generally hydrophobic with low water solubilites (i.e. 0.002-0.5 ng/L) but have high solubilities in most organic solvents, oils and fats. They generally have low vapor pressures at room temperature. They generally have dielectric constants of 2.25-2.8, very high thermal conductivity and high flash points. The PCBs generally have densities varying from 1.1 to 1.7 Kg/L and generally as the degree of chlorination increases the melting point and lipophilicity increase while vapor pressure and water solubility decrease. PCBs do not easily break down or degrade and are resistant to acids, bases, oxidation, hydrolysis, and temperature change.

PCBs are derived from biphenyl ($C_{12}H_{10}$ or $(C_6H_5)_2$). In PCBs some of the hydrogen atoms in biphenyl are replaced by chlorine atoms. There are over 200 different chemical compounds in which one to ten chlorine atoms can replace hydrogen atoms. PCBs are typically used as mixtures of compounds and are given the single identifying CAS number 1336-36-3. Generally PCBs fall into two distinct categories, referred to as coplanar or non-ortho-substituted arene substitution patterns and noncoplanar or ortho-substituted cogeners. In terms of the present disclosure, the at least on polychlorinated biphenyl may be coplanar, noncoplanar, or mixtures thereof. Exemplary suitable polychlorinated biphenyls include, but are not limited to, monochlorobiphenyls (1 Cl, 3 congeners), dichlorobiphenyls (2 Cl, 12 congeners), trichlorobiphenyls (3 Cl, 24 congeners), tetrachlorobiphenyls (4 Cl, 42 congeners), pentachlorobiphenyls (5 Cl, 46 congeners), hexachlorobiphenyls (6 Cl, 42 congeners), heptachlorobiphenyls (7 Cl, 24 congeners), octachlorobiphenyls (8 Cl, 12 congeners), nonachlorobiphenyls (9 Cl, 3 congeners), decachlorobiphenyls (10 Cl, 1 congener), PCB 77, PCB 10, PCB 156, PCB 81, PCB 114, PCB 157, PCB 126, PCB 118, PCB 167, PCB 169, PCB 123, PCB 189, and the like.

In certain embodiments, the at least one polychlorinated biphenyl may be a commercial polychlorinated biphenyl mixture. Exemplary, commercial polychlorinated biphenyl mixtures may include, but are not limited to, Ascarel (Brazil), Delor (Czechoslovakia), Phenoclor, Pyralene (France), Clophen (Germany), Apirolio, Fenclor (Italy), Kanechlor, Santotherm, Pyroclor (Japan), Sovol, Sovtol (USSR), Askarel, Aroclor xxxx, Asbestol, Bakola 131, Chlorextol, Hydol, Inerteen, Noflamol, Pyranol/Pyrenol, Chlorinol, Saf-T-Kuhl, Therminol FR Series, and the like. In a preferred embodiment, the at least one polychlorinated biphenyl is a commercial polychlorinated biphenyl mixture, most preferably an Aroclor.

In a preferred embodiment, the polychlorinated biphenyl (PCB) refers to an Aroclor mixture. The only North American producer, Monsanto Company, marketed PCBs under the trade name Aroclor from 1930 to 1977. These were sold under trade names followed by a 4-digit number. Generally, the first two digits refer to the number of carbon atoms in the biphenyl skeleton (often for PCBs this is 12); the second two numbers indicate the percentage of chlorine by mass in the mixture. For example, Aroclor 1260 has 12 carbon atoms and contains 60% chlorine by mass. In a preferred embodiment, the at least one polychlorinated biphenyl is at least one selected from the group consisting of Aroclor 1260, Aroclor 1254, and Aroclor 1242, preferably at least one selected from the group consisting of Aroclor 1260 and Aroclor 1254. In a preferred embodiment, the at least one polychlorinated biphenyl is an Aroclor mixture which has 40-70% chlorine by mass, preferably 45-66% chlorine by mass, preferably 50-62% chlorine by mass, preferably 55-60% chlorine by mass.

Non-limiting examples of aqueous solutions (i.e. polychlorinated biphenyl contaminated aqueous solutions), water sources and systems include, but are not limited to, surface water that collects on the ground or in a stream, aquifer, river, lake, reservoir or ocean, ground water that is obtained by drilling wells, run-off, industrial water, public water storage towers, public recreational pools and/or bottled water. In a preferred embodiment, the aqueous solution is seawater or salt water from a sea or ocean having a salinity of 10-100 g/L, preferably 15-80 g/L, preferably 20-60 g/L, preferably 25-50 g/L, preferably 30-40 g/L or about 35 g/L. In a preferred embodiment, the aqueous solution has a pH in the range of 4-7, preferably 4.25-6.5, preferably 4.5-6.0, preferably 4.75-5.5, preferably 4.8-5.2, or about 5.0. In a preferred embodiment, the polychlorinated biphenyl is present in the aqueous solution in an amount in the range of 0.1-1.5 ppm, preferably 0.2-1.25 ppm, preferably 0.3-1.0 ppm, preferably 0.4-0.8 ppm, preferably 0.45-0.60 ppm, or about 0.50 ppm.

As used herein, titanium dioxide, also known as titanium (IV) oxide or titania, is a naturally occurring or synthetic oxide of titanium with the chemical formula $TiO_2$. Titanium dioxide occurs in nature as the minerals rutile (tetragonal crystal system), anatase (tetragonal crystal system) and brookite (orthorhombic crystal system) and additionally as two high pressure forms, a monoclinic baddeleyite-like form (7 coordinated Ti) and an orthorhombic $\alpha$-$PbO_2$-like form, one known as akaogiite and is an extremely rare mineral. It is mainly source from ilmenite ore or rutile ore. Titanium dioxide has eight modifications, in addition to rutile, anatase, and brookite, three metastable phases can be produced synthetically (monoclinic, tetragonal and orthorhombic), and five high-pressure forms ($\alpha$-$PbO_2$-like, baddeleyite-like, cotunnite-like, orthorhombic OI, and cubic phases) also exist.

The titanium dioxide nanoparticles, carbon modified titanium dioxide nanoparticles of the present disclosure and/or the photocatalyst comprising carbon modified titanium dioxide nanoparticles of the present disclosure in any of their embodiments may be crystalline or polycrystalline, preferably nanocrystalline. The titanium dioxide may be in an anatase phase, a rutile phase, a brookite phase, or a combination thereof. Preferably the titanium dioxide nanoparticles, carbon modified titanium dioxide nanoparticles, and/or photocatalyst comprising carbon modified nanoparticles are in an anatase phase. In certain embodiments, the titanium dioxide nanoparticles, carbon modified titanium dioxide nanoparticles of the present disclosure and/or the photocatalyst comprising carbon modified titanium dioxide nanoparticles comprise at least 10 wt % of the anatase phase, preferably at least 20 wt %, preferably at least 40 wt %, preferably at least 60 wt %, preferably at least 80 wt %, preferably at least 85 wt %, preferably at least 90 wt %, preferably at least 95 wt % of the anatase phase based on the total weight of the titanium dioxide nanoparticles carbon modified titanium dioxide nanoparticles of the present disclosure and/or the photocatalyst comprising carbon modified titanium dioxide nanoparticles. In certain embodiments, the proportion of each phase may be determined from an XRD pattern. In certain embodiments, the amount of the rutile phase may be below the detection limit (e.g. less than 3 wt %) of the XRD instrumentation. In certain embodiments, the titanium dioxide nanoparticles, carbon modified titanium dioxide nanoparticles of the present disclosure and/or the photocatalyst comprising carbon modified titanium dioxide nanoparticles may be amorphous (i.e. lacking a crystalline structure).

Anatase and rutile have the same symmetry, tetragonal 4/m 2/m 2/m, despite having different structures. In rutile, the structure is based on octahedrons of titanium oxide which share two edges of the octahedron with other octahedrons and form chains. It is the chains themselves which are arranged into a four-fold symmetry. In anatase, the octahedrons share four edges hence the four fold axis. Crystals of anatase are very distinctive and form the eight faced tetragonal dipyramids that come to sharp elongated points. $TiO_2$ preferably has a body centered tetragonal unit cell, with unit cell parameters a=b=3.776 Å, c=9.486 Å. The titanium cations have a coordination number of 6 meaning they are surrounded by an octahedron of 6 oxygen atoms. The oxygen anions have a coordination number of 3 resulting in trigonal planar coordination and distorted ccp O with Ti in a portion (half) of Oh holes.

As used herein, carbon modified preferably refers to elemental carbon. In a preferred embodiment the carbon modified titanium dioxide nanoparticles comprise elemental carbon incorporated into the lattice structure of the titanium dioxide. For example, the elemental carbon may be embedded between titanium dioxide molecules to become integral with the lattice. Alternatively, the elemental carbon may be embedded into the pores of the titanium dioxide lattice and thus not integral to the titanium dioxide lattice. In certain alternative embodiments, the elemental carbon is not incorporated into the lattice structure of titanium dioxide and may be adsorbed on the surface (e.g. by van der Waals and/or electrostatic forces) of the titanium dioxide nanoparticles. Carbon can form different structures with $TiO_2$, such as for example carbon doped $TiO_2$, carbon coated $TiO_2$ and composites of $TiO_2$ and carbon. Carbon may be present as a layer on the surface of $TiO_2$ as well as present as porous carbon in composites with $TiO_2$. In a preferred embodiment, the carbon doping replaces Ti or oxygen with a carbon atom. Additionally the carbon may be in the form of a carbide or an interstitial carbon atom or structure between $TiO_2$ layers. Preferably carbon is present as interstitial or substitutional carbon in carbon doped or carbon modified $TiO_2$. In a preferred embodiment, the carbon modified titanium dioxide nanoparticles are formed by a sonicated sol-gel method.

It is equally envisaged that the titanium dioxide nanoparticles, carbon modified titanium dioxide nanoparticles of the present disclosure and/or the photocatalyst comprising carbon modified titanium dioxide nanoparticles of the present disclosure may further comprise or may be adapted to comprise additional carbonaceous materials in addition to or in lieu of elemental carbon. Exemplary suitable carbonaceous materials include, but are not limited to, graphite powder, graphene, acetylene black (AB), obtained by controlled combustion of acetylene in inert atmosphere or chemical decomposition, carbon black, an amorphous material obtainable by the incomplete combustion of heavy petroleum fractions, colloidal graphite, hexagonal carbon with extremely fine flakes and enhanced conductivity, both natural and synthetic forms of diamond applied as fine powders, soot, activated charcoal, coal ("black coal"), lignite ("brown coal"), glassy carbon (GC), fullerene (C-60), carbon nanomaterials (carbon nanotubes, CNTs, carbon nanohorns, carbon nanoparticles, carbon nanofibers), porous carbon foam, porous carbon microspheres, template carbon, ordered mesoporous carbon (OMC) and the like.

As used herein, the atomic ratio is a measure of the ratio of the number of atoms of one kind (i.e. titanium, Ti) to another kind (i.e. carbon, C) and the closely related concept atomic percent and/or atomic percentage (at. %) gives the percentage of one kind of atom (i.e. Ti, C, or oxygen, O) relative to the total number of atoms. Further the molecular equivalents of these concepts are the molar fraction or molar percent. In a preferred embodiment, the carbon modified titanium dioxide nanoparticles of the present disclosure or the photocatalyst comprising carbon modified titanium dioxide nanoparticles of the present disclosure in any of their embodiments has a Ti:C atomic ratio in the range of 3:1 to 6:1, preferably 3:1 to 5:1, preferably 3:1 to 4.5:1, preferably 3:1 to 4.0:1, preferably 3.1:1 to 3.8:1, preferably 3.2:1 to 3.5:1, preferably 3.3:1 to 3.4:1 or about 3.33:1. In a preferred embodiment, the carbon modified titanium dioxide nanoparticles of the present disclosure or the photocatalyst comprising carbon modified titanium dioxide nanoparticles of the present disclosure in any of their embodiments has a O:C atomic ratio in the range of 6:1 to 12:1, preferably 6:1 to 10:1, preferably 6:1 to 9:1, preferably 6:1 to 8:1, preferably 6.2:1 to 7.6:1, preferably 6.4:1 to 7:1, preferably 6.6:1 to 6.8:1 or about 6.7:1. In a preferred embodiment, the carbon modified titanium dioxide nanoparticles of the present disclosure or the photocatalyst comprising carbon modified titanium dioxide nanoparticles of the present disclosure in any of their embodiments has a 5-15% atomic percentage of carbon relative to the total atomic percentage of the carbon modified titanium dioxide nanoparticles or the total atomic percentage of the photocatalyst comprising carbon modified titanium dioxide nanoparticles, preferably 6-14% atomic percentage, preferably 7-13% atomic percentage, preferably 8-12% atomic percentage, preferably 8.25-11% atomic percentage, preferably 8.5-10% atomic percentage, preferably 8.75-9.5% atomic percentage, or about 9% atomic percentage of carbon relative to the total atomic percentage of the carbon modified titanium dioxide nanoparticles or the total atomic percentage of the photocatalyst comprising carbon modified titanium dioxide nanoparticles In a preferred embodiment, the titanium dioxide nanoparticles, carbon modified titanium dioxide nanoparticles of the present disclosure and/or the photocatalyst comprising carbon modified titanium dioxide nanoparticles is substantially spherical (e.g. oval or oblong in shape). In certain other embodiments, the titanium dioxide nanoparticles, carbon modified titanium dioxide nanoparticles of the present disclosure and/or the photocatalyst comprising carbon modified titanium dioxide nanoparticles may be of any shape or morphology that provides a desired photocatalytic activity. In some embodiments, this may be in the form of at least one shape such as a sphere, a rod, a cylinder, a rectangle, a triangle, a pentagon, a hexagon, a prism, a disk, a platelet, a cube, a cuboid, and/or an urchin (e.g. a globular particle possessing a spiky or uneven surface).

In certain embodiments, the titanium dioxide nanoparticles, carbon modified titanium dioxide nanoparticles of the present disclosure and/or the photocatalyst comprising carbon modified titanium dioxide nanoparticles may be uniform. As used herein, the term "uniform" refers to no more than 10%, preferably no more than 5%, preferably no more than 4%, preferably no more than 3%, preferably no more than 2%, preferably no more than 1% of the distribution of the titanium dioxide nanoparticles, carbon modified titanium dioxide nanoparticles of the present disclosure and/or the photocatalyst comprising carbon modified titanium dioxide nanoparticles having a different shape. For example, the titanium dioxide nanoparticles, carbon modified titanium dioxide nanoparticles of the present disclosure and/or the photocatalyst comprising carbon modified titanium dioxide nanoparticles are uniform and nanocrystalline having no more than 1% in an amorphous phase. As used herein, the term "non-uniform" refers to more than 10% of the distribution of the titanium dioxide nanoparticles, carbon modified titanium dioxide nanoparticles of the present disclosure and/or the photocatalyst comprising carbon modified titanium dioxide nanoparticles having a different shapes. In certain embodiments, the titanium dioxide nanoparticles, carbon modified titanium dioxide nanoparticles of the present disclosure and/or the photocatalyst comprising carbon modified titanium dioxide nanoparticles are non-uniform.

As used herein, "dispersity" is a measure of the heterogeneity of sizes of molecules, particles, or crystals in a mixture. In probability theory and statistics, the coefficient of variation (CV) also known as relative standard deviation (RSD) is a standardized measure of dispersion of a probability distribution. It is expressed as a percentage and may be defined as the ratio of the standard deviation ($\sigma$) to the mean ($\mu$, or its absolute value $|\mu|$). The coefficient of variation or relative standard deviation is widely used to express precision and/or repeatability. It may show the extent of variability in relation to the mean of a population. In a preferred embodiment, the carbon modified titanium dioxide nanoparticles of the present disclosure or the photocatalyst comprising carbon modified titanium dioxide nanoparticles of the present disclosure in any of their embodiments have a narrow size dispersion, i.e. monodispersity. As used herein, "monodisperse", "monodispersed", and/or "monodispersity" refer to carbon modified titanium dioxide nanoparticles or crystals of the present disclosure or the photocatalyst comprising carbon modified titanium dioxide nanoparticles or crystals of the present disclosure which have a CV or RSD of less than 30%, preferably less than 25%, preferably less than 20%, preferably less than 13%, preferably less than 32%, preferably less than 10%, preferably less than 8%, preferably less than 5%.

In a preferred embodiment, the carbon modified titanium dioxide nanoparticles of the present disclosure or the photocatalyst comprising carbon modified titanium dioxide nanoparticles of the present disclosure in any of their embodiments are monodisperse with a coefficient of variation or relative standard deviation (ratio of the crystalline size standard deviation to the crystalline size mean) of less than 15%, preferably less than 12%, preferably less than 10%, preferably less than 9%, preferably less than 8%, preferably less than 7%, preferably less than 6%, preferably less than 5%, preferably less than 4%, preferably less than 2%. In a preferred embodiment, the carbon modified titanium dioxide nanoparticles of the present disclosure or the photocatalyst comprising carbon modified titanium dioxide nanoparticles of the present disclosure in any of their embodiments are monodisperse and have a crystalline size distribution in a range of 75% of the average crystalline size to 125% of the average crystalline size, preferably 80-120%, preferably 85-115%, preferably 86-114%, preferably 87-113%, preferably 88-112%, preferably 89-111%, preferably 90-110%, preferably 95% of the average crystalline size to 105% of the average crystalline size.

As used herein, "crystallite size", "crystalline size" and/or "crystal size" refers to a Scherrer derived particle size or crystal size. A Scherrer derived particle size or crystal size relates the mean (volume average) crystal or particle size of a powder to the broadening of its powder diffraction peaks. In a preferred embodiment, the carbon modified titanium dioxide nanoparticles of the present disclosure or the photocatalyst comprising carbon modified titanium dioxide nanoparticles of the present disclosure in any of their embodiments have an average crystal size of 25-35 nm, preferably 26-34 nm, preferably 27-33.5 nm, preferably 28-33 nm, preferably 29-32.5 nm, preferably 30-32 nm, preferably 31-31.8 nm, or about 31.5 nm. In a preferred embodiment, the carbon modified titanium dioxide nanoparticles of the present disclosure or the photocatalyst comprising carbon modified titanium dioxide nanoparticles of the present disclosure in any of their embodiments have an average crystal size that is at least 20 nm smaller than the average crystal size of substantially similar titanium dioxide nanoparticles lacking the carbon modification, preferably at least 18 nm smaller, preferably at least 16 nm smaller, preferably at least 14 nm smaller, preferably at least 12 nm smaller, preferably at least 10 nm smaller, preferably at least 8 nm smaller, preferably at least 6 nm smaller, preferably at least 5 nm smaller than the average crystal size of substantially similar titanium dioxide nanoparticles lacking the carbon modification. As used herein, the diameter or average particle or crystal size may refer to the longest linear distance measured from one point on the particle or crystal through the center of the particle or crystal to a point directly across from it.

As used herein, band gap energy, band gap, and/or energy gap refers to an energy range in a solid where no electron states can exist. In graphs of the electronic band structure of solids, the band gap generally refers to the energy difference (in electron volts) between the top of the valence band and the bottom of the conduction band in insulators and/or semiconductors. It is generally the energy required to promote a valence electron bound to an atom to become a conduction electron, which is free to move within the crystal lattice and serve as a charge carrier to conduct electric current. It is closely related to the HOMO/LUMO gap in chemistry. In a preferred embodiment, the carbon modified titanium dioxide nanoparticles of the present disclosure or the photocatalyst comprising carbon modified titanium dioxide nanoparticles of the present disclosure in any of their embodiments have a band gap energy or band gap value of less than 3.0 eV, preferably less than 2.9 eV, preferably less than 2.8 eV, preferably less than 2.6 eV, preferably less than 2.4 eV, preferably less than 2.2 eV, preferably less than 2.0 eV, preferably less than 1.8 eV, preferably less than 1.6 eV, preferably less than 1.5 eV. In a preferred embodiment, the carbon modified titanium dioxide nanoparticles of the present disclosure or the photocatalyst comprising carbon modified titanium dioxide nanoparticles of the present disclosure in any of their embodiments have a band gap energy or band gap value in the range of 1.4-2.0 eV, preferably 1.5-1.95 eV, preferably 1.6-1.9 eV, preferably 1.7-1.85 eV, preferably 1.75-1.825 eV, preferably 1.78-1.82 eV, or about 1.80 eV. In a preferred embodiment, the carbon modified titanium dioxide nanoparticles of the present disclosure or the photocatalyst comprising carbon modified titanium dioxide nanoparticles of the present disclosure in any of their embodiments have a band gap energy or band gap value that is greater than 2.0 eV less than the band gap energy or band gap value of substantially similar titanium dioxide nanoparticles lacking the carbon modification, preferably greater than 1.8 eV less, preferably greater than 1.6 eV less, preferably greater than 1.4 eV less, preferably greater than 1.2 eV less, preferably greater than 1.0 eV less, preferably greater than 0.8 eV less than the band gap energy or band gap value of substantially similar titanium dioxide nanoparticles lacking the carbon modification.

In certain embodiments, the carbon modified titanium dioxide nanoparticles of the present disclosure or the photocatalyst comprising carbon modified titanium dioxide nanoparticles of the present disclosure in any of their embodiments and/or the aqueous solution may further comprise additives, preferably to increase the photolysis of a polychlorinated biphenyl (such as for example to increase $H_2$ and/or $O_2$ production). Exemplary chemical additives include, but are not limited to, electron donors (i.e. organic hydrocarbons or inorganic ions such as $S^{2-}/SO_3^{2-}$, $Ce^{4+}/Ce^{3+}$, and $IO_3^-/I^-$) and carbonate salts (i.e. $HCO_3^-$, $CO_3^-$, and $C_2O_6^{2-}$) which may suppress the reverse reaction. Furthermore, the carbon modified titanium dioxide nanoparticles of the present disclosure or the photocatalyst comprising carbon modified titanium dioxide nanoparticles of the present disclosure in any of their embodiments may be modified, preferably to increase the photolysis of a polychlorinated biphenyl. Exemplary modifications include, but are not limited to, noble metal loading (i.e. Pt, Au, Pd, Rh, Ni, Cu, and Ag), ion doping including metal ion doping (i.e. Fe, Mo, Ru, Os, Re, V, Rh, Cr, Mn, and Co) and anion doping (i.e. N, F, C, N, P, O, and S), sensitization including dye sensitization (i.e. thiazines, hiazines, phenazines, xanthenes, acridines, and triphenyl methane derivatives) and composite semiconductors and/or metal ion implantation (i.e. V-ions, Mn-ions, Ni-ions, Ar-ions, Mg-ions, Cr-ions, Ti-ions, and Fe-ions).

In a preferred embodiment, the carbon modified titanium dioxide nanoparticles of the present disclosure or the photocatalyst comprising carbon modified titanium dioxide nanoparticles of the present disclosure in any of their embodiments are dispersed in the aqueous solution, preferably homogeneously dispersed and/or dissolved in the aqueous solution. In a preferred embodiment, the carbon modified titanium dioxide nanoparticles of the present disclosure or the photocatalyst comprising carbon modified titanium dioxide nanoparticles of the present disclosure in any of their embodiments are present in an amount in the range of 0.1-1.5 g of carbon modified titanium dioxide nanoparticles per 1.0 L of the aqueous solution, preferably 0.2-1.25 g, preferably 0.3-1.0 g, preferably 0.4-0.75 g, preferably 0.45-0.6 g, or about 0.5 g of carbon modified titanium dioxide nanoparticles per 1.0 L of the aqueous solution.

In certain embodiments, it is equally envisaged the carbon modified titanium dioxide nanoparticles of the present disclosure or the photocatalyst comprising carbon modified titanium dioxide nanoparticles of the present disclosure in any of their embodiments may be present as a coating in the system, preferably on the tray of the system oriented towards the light source, in addition to or in lieu of dispersed in the aqueous solution. The photocatalyst and/or carbon modified titanium dioxide nanoparticles may suitably be deposited on the system, preferably on the tray of the system oriented towards the light source from solution or suspension, or by other alternative deposition techniques including, but not limited to, pulsed layer deposition, physical vapor deposition, and/or atomic layer deposition. In certain embodiments, the coating may be present and have an average thickness of 1-1000 µm, preferably 10-500 µm, preferably 20-450 µm, preferably 40-400 µm, preferably 60-350 µm, preferably 80-320 µm, preferably 100-300 µm, preferably 120-250 µm, preferably 140-200 µm. In certain embodiments, the coating may be present and cover at least 10% of the surface area of the tray oriented towards the light source or irradiated/exposed surface area of the tray, preferably at least 15%, preferably at least 20%, preferably at least 25%, preferably at least 30%, preferably at least 40%, preferably at least 50%, preferably at least 60%, preferably at least 70%, preferably at least 75%, preferably at least 80%, preferably at least 85%, preferably at least 90% of the surface area of the tray oriented towards the light source or irradiated/exposed surface area of the tray.

In one aspect of the system, a tray is present and is oriented at a tilt angle from the horizontal comprising a distributor end and an opposing collector end located at a lower vertical height than the distributor end, wherein the tray is configured to flow the aqueous solution from the distributor end to the collector end while exposing the aqueous solution to the light source forming a remediated aqueous solution comprising a second amount of at least one polychlorinated biphenyl.

The tray may be constructed of a material, such as metal, plastic, ceramic or glass that can withstand the temperatures and pressures associated with the operation of the system. In a preferred embodiment, the tray is fabricated in at least one selected from the group consisting of steel, stainless steel, glass-lined steel, glass or exotic alloy. In a more preferred embodiment the tray is fabricated of stainless steel, a steel alloy with a minimum of 10.5% chromium content by mass. In a most preferred embodiment, the tray is fabricated of an austenitic (200 or 300 series) stainless steel, most preferably 316 grade stainless steel. The 316 grade stainless steel is also referred to as A4 stainless and/or marine grade stainless is used primarily for its increased resistance to corrosion. A typical composition may include 15-20 wt % chromium and 5-15 wt % nickel, more preferably 17-19 wt % chromium and 9-11 wt % nickel, or about 18 wt % chromium and 10 wt % nickel (i.e. 18/10 stainless).

In a preferred embodiment the tray has a total volume of 1-10000 L, preferably 5-5000 L, preferably 10-1000 L, preferably 12-500 L, preferably 15-250 L, preferably 20-100 L. In a preferred embodiment, the tray has an irradiated or exposed to the light source surface area of 0.25-20 m$^2$, preferably 0.5-15 m$^2$, preferably 0.75-10 m$^2$, preferably 1-5 m$^2$, preferably 1.5-3 m$^2$. In a preferred embodiment, the tray is rectangular with a length (i.e. shortest linear distance from the distributor end to the opposing collector end) that is 1-5 times the width, preferably 1.25-4 times the width, preferably, 1.5-3 times the width, preferably 1.75-2.5 times the width, or about 2 times the width. In certain embodiments the tray may further comprise side walls having a height of 1-50 cm, preferably 2-40 cm, preferably 4-35 cm, preferably 6-30 cm, preferably 8-25 cm, preferably 10-20 cm. In a preferred embodiment, the side walls are 0.01-0.3 times the width of the tray, preferably 0.05-0.25, preferably 0.08-0.2, preferably 0.1-0.15 times the width of the tray.

In a preferred embodiment, the tray is planar. In another embodiment, the tray may be convex or concave and the convex or concave face of the tray may be oriented towards the horizontal opposing the light source or opposing the horizontal towards the light source. The topology and morphology of the tray may also be varied to fit the application and is not viewed as particularly limiting. In a preferred embodiment, the tray is flat or smooth. In another embodiment, the surface of the tray is ridged, threaded, and/or corrugated describing a series of parallel ridges or furrows. In certain embodiments, the height of the ridges from the basal plane of the tray is less than 20 cm, preferably less than 15 cm, preferably less than 10 cm, preferably less than 8 cm, preferably less than 5 cm, preferably less than 3 cm. In another embodiment, one surface and/or side of the tray may be flat and a second surface and/or side of the tray may be corrugated. In this case, the corrugated side is preferably oriented opposing the horizontal towards the light source and the flat surface is preferably oriented towards the horizontal opposing the light source; however, the inverse may also be sufficient. In one embodiment, more the system may comprise more than one tray in sequence and/or in parallel.

In a preferred embodiment, the tray is oriented at a tilt angle form the horizontal. In a preferred embodiment, the tilt angle from the horizontal is 1-89° measured from a horizontal axis, preferably 2-80°, preferably 3-70°, preferably 4-60°, more preferably 5-40°, more preferably 10-35°, more preferably 15-30°, more preferably 18-28°, more preferably 20-25°, or about 22° measured from the horizontal. In certain embodiments, the tray is fixed and set at a single angle in the ranges described above. In certain additional embodiments, the attachment of the tray to the system may further comprise a pivot, a hinge, attachment means and/or bearing that allows a limited range of motion or angle of rotation between the tray and the horizontal axis. Exemplary types of hinges include, but are not limited to, barrel hinges, pivot hinges, butt/mortise hinges, case hinges, continuous (piano) hinges, concealed hinges, butterfly (parliament) hinges, flag hinges, strap hinges, H hinges, HL hinges and the like. In certain embodiments, during operation of the system the angle is fixed and set at a single angle within the ranges described above and can be adjusted and fixed when the system is not in operation. In certain alternative embodiments, during operation of the system the angle may have a free range of motion of less than 15°, preferably less than 10°, preferably less than 5°, preferably less than 2°, preferably less than 1°.

In one aspect of the system, a pump is present and the vessel is configured to deliver the aqueous solution through the pump to the distributor end of the tray. As used herein, a pump refers to a device that moves fluids (e.g., liquids) by mechanical action. Pumps may be classified into three major groups according to the method they use to move the fluid: direct lift, displacement, and gravity pumps. Pumps operate by a mechanism (e.g., reciprocating or rotary) and consume energy to perform mechanical work by moving the fluid. Pumps operate via many energy sources including manual operation, electricity and engines and com in many sizes from microscopic to large industrial pumps. Exemplary suitable water and/or oil pumps include, but are not limited to, positive displacement pumps (rotary, reciprocating, linear), impulse pumps, velocity pumps, gravity pumps, steam pumps, valveless pumps, centrifugal pumps, gear pumps, screw pumps, rotary vane pumps, plunger pumps, diaphragm pumps, piston pumps, radial piston pumps, rotary lobe pumps, progressive cavity pumps, rotary gear pumps, hydraulic pumps, peristaltic pumps, rope pumps, flexible impeller pumps, radial flow pumps, axial flow pumps, mixed flow pumps, educator jet pumps, and the like. In certain embodiments the pump is a variable flow pump, preferably a variable displacement pump. As used herein, a variable displacement pump is a device that converts mechanical energy to hydraulic (fluid) energy. The displacement, or amount of fluid pumped per revolution of the pump's input shaft can be varied while the pump is running. In one embodiment, the pump may optionally be included and the system may rely upon gravity feeding entirely including gravity feeding to the distributor end as well as gravity feeding for the flow from the distributor end to the collector end.

In one aspect of the system, a light source that emits or irradiates light which comprises light which has a wavelength in the ultraviolet or visible region is present and the tray is configured to flow the aqueous solution from the distributor end to the collector end while exposing the aqueous solution to the light source forming a remediated aqueous solution comprising a second amount of at least one polychlorinated biphenyl. In a preferred embodiment, the light source is the sun and the emitted or irradiating light or energy is naturally occurring sunlight, solar light, and/or solar energy.

In certain embodiments, the exposing or irradiating may be performed by a light source internal or external to the tray an may provide the photon energy necessary to activate the carbon modified titanium dioxide nanoparticles of the present disclosure or the photocatalyst comprising carbon modified titanium dioxide nanoparticles of the present disclosure in any of their embodiments as a photocatalyst. In a preferred embodiment, the light source has a wavelength of 100-1000 nm, preferably 200-900 nm, preferably 250-850 nm, preferably 300-800 nm, preferably 350-700 nm, preferably 400-700 nm. In a preferred embodiment, the light source is naturally occurring solar light and the irradiating or exposing is performed with natural solar light, preferably natural solar light having a wavelength of 300-800 nm, preferably 385-740 nm, preferably 400-700 nm. In certain embodiments, the light source has a wavelength of 300-800 nm, preferably 315-400 nm. It is equally envisaged that the light source may be from a wide variety of known light sources, including, but not limited to, natural solar sunlight, UV light, laser light, incandescent light, and the like. Exemplary light sources include, but are not limited to, a xenon lamp, a UV fluorescent lamp, a mercurial lamp, a metal halide lamp, an LED lamp, a halogen lamp, the sun, a solar simulator, and the like. In certain embodiments, two or more light sources may be used.

In a preferred embodiment, the first amount of at least one polychlorinated biphenyl is greater than the second amount of at least one polychlorinated biphenyl. In a preferred embodiment the first amount of at least one polychlorinated biphenyl is at least 1% greater than the second amount of at least one polychlorinated biphenyl, preferably at least 2% greater, preferably at least 5% greater, preferably at least 10% greater, preferably at least 15% greater, preferably at least 20% greater, preferably at least 25% greater, preferably at least 30%, greater, preferably at least 35% greater, preferably at least 40% greater, preferably at least 45% greater, preferably at least 50% greater than the second amount of at least one polychlorinated biphenyl.

In certain embodiments, the closed-loop system may further comprise one or more valves. As used herein, a valve is a device that regulates, directs or controls the flow of a fluid (gases, liquids, solutions, fluidized solids, or slurries) by opening, closing, or partially obstructing various passageways. Valves vary widely in form, size and application. Valves are quite diverse and may be classified into a number of basic types including, but not limited to hydraulic, pneumatic, manual, solenoid, and motor. In certain embodiments, the position and operation of the valves can be manually operated to regulate the flow of fluid. Alternatively, the position of the valve can be controlled via circuitry based on changing demands through the system and/or time of day. In certain embodiments, the valves may refer to two port valves, three port valves, four point valves, and mixtures thereof. In certain embodiments, the valves may refer to a control valve, an expansion valve, check valves, relief valves, and mixtures thereof. For example, the closed-loop system may comprise a by-pass valve to regulate and/or adjust the flow of fluid through the system.

According to another aspect, the present disclosure relates to a method for remediating an aqueous solution comprising at least one polychlorinated biphenyl employing the system of the present disclosure in any of its embodiments, the method comprising i) flowing the aqueous solution from the vessel through the pump to the distributor end of the tray, ii) flowing the aqueous solution from the distributor end of the tray to the collector end of the tray via gravity while exposing the aqueous solution to the light source thereby photocatalytically degrading or mineralizing the at least one polychlorinated biphenyl to obtain the remediated aqueous solution, and iii) returning the remediated aqueous solution to the vessel. In a preferred embodiment, the aqueous solution, the remediated aqueous solution, or both continuously circulates in a closed-loop circuit.

In certain embodiments, the remediated aqueous solution is optionally returned to the vessel, alternatively it may be removed from the system or undergo further processing in a variety of additional components.

In a preferred embodiment, greater than 70% by weight of the polychlorinated biphenyl relative to die first amount of the polychlorinated biphenyl is photocatalytically degraded or mineralized, preferably greater than 75%, preferably greater than 80%, preferably greater than 85%, preferably greater than 90%, preferably greater than 95% after the exposing is carried out for a time period of 10-60 minutes, preferably 15-50 minutes, preferably 20-40 minutes, preferably 22-38 minutes, preferably 24-36 minutes, preferably 26-34 minutes, preferably 28-32 minutes.

In a preferred embodiment, greater than 90% by weight of the polychlorinated biphenyl relative to the first amount of the polychlorinated biphenyl is photocatalytically degraded or mineralized, preferably greater than 92%, preferably greater than 94%, preferably greater than 96%, preferably greater than 98%, preferably greater than 99%, preferably greater than 99.5% after the exposing is carried out for a time period of less than 60 minutes, preferably less than 55 minutes, preferably less than 50 minutes, preferably less than 45 minutes, preferably less than 40 minutes, preferably less than 38 minutes, preferably less than 36 minutes, preferably less than 34 minutes, preferably less than 32 minutes, preferably less than 30 minutes.

In a preferred embodiment, at least 50% by weight of the polychlorinated biphenyl relative to the first amount of the polychlorinated biphenyl, preferably at least 52%, preferably at least 54%, preferably at least 56%, preferably at least 58%, preferably at least 60%, preferably at least 65%, preferably at least 70%, preferably at least 75%, preferably at least 80%, preferably at least 85% is photocatalytically degraded or mineralized after the exposing is carried out for a time period of less than 20 minutes, preferably less than 18 minutes, preferably less than 16 minutes, preferably less than 14 minutes, preferably less than 12 minutes, preferably less than 10 minutes, preferably less than 8 minutes and this time period is 40-60% less than, preferably 42-58% less than, preferably 44-56% less than, preferably 46-54% less than, preferably 48-52% less than, preferably 49-51% less than a time period wherein at least 50% by weight of the polychlorinated biphenyl relative to the first amount of the polychlorinated biphenyl, preferably at least 52%, preferably at least 54%, preferably at least 56%, preferably at least 58%, preferably at least 60%, preferably at least 65%, preferably at least 70%, preferably at least 75%, preferably at least 80%, preferably at least 85% is photocatalytically degraded or mineralized by exposure in a substantially similar method employing a substantially similar system in a substantially similar manner with titanium dioxide nanoparticles which have a Ti:C atomic ratio of greater than 50:1, preferably greater than 60:1, preferably greater than 70:1, preferably greater than 80:1, preferably greater than 90:1, preferably greater than 100:1, preferably greater than 200:1, preferably greater than 500:1 or substantially similar titanium dioxide nanoparticles lacking the carbon modification.

According to another aspect, the present disclosure relates to a method for remediating an aqueous solution comprising at least one polychlorinated biphenyl, the method comprising i) contacting the photocatalyst of the present disclosure in any of its embodiments with the aqueous solution comprising at least one polychlorinated biphenyl to form a treated aqueous solution and ii) exposing the treated aqueous solution to a light source having a wavelength in the ultraviolet or visible region thereby photocatalytically degrading or mineralizing the at least one polychlorinated biphenyl to form a remediated aqueous solution.

In certain embodiments, the methods may be carried out employing the system described herein or without employing the system described herein. The method may be carried out in tanks, containers, or small scale applications in both batch mode and fixed-bed or column mode when the system of the present disclosure is not employed. In a preferred embodiment, the contacting and exposing is carried out for a time period of 1-240 minutes, preferably 2-210 minutes, preferably 3-180 minutes, preferably 4-150 minutes, preferably 5-120 minutes, preferably 10-60 minutes and at a temperature of 10-100° C., preferably 20-80° C., preferably 25-60° C., preferably 25-40° C., preferably 25-30° C.

In a preferred embodiment, greater than 70% by weight of the polychlorinated biphenyl is photocatalytically degraded or mineralized, preferably greater than 75%, preferably greater than 80%, preferably greater than 85%, preferably greater than 90%, preferably greater than 95% after the exposing is carried out for a time period of 1-25 minutes, preferably 2-20 minutes, preferably 3-18 minutes, preferably 4-15 minutes, preferably 5-10 minutes.

In a preferred embodiment, a removal efficiency of the polychlorinated biphenyl is at least 2 times greater than a removal efficiency of a substantially similar method performed in a substantially similar manner, preferably at least 2.2 times greater, preferably at least 2.4 times greater, preferably at least 2.6 times greater, preferably at least 2.8 times greater, preferably at least 3 times greater, preferably at least 4 times greater, preferably at least 5 times greater than a removal efficiency of a substantially similar method performed in a substantially similar manner with a photocatalyst which has a Ti:C atomic ratio of greater than 50:1, preferably greater than 60:1, preferably greater than 70:1, preferably greater than 80:1, preferably greater than 90:1, preferably greater than 100:1, preferably greater than 200:1, preferably greater than 500:1 or substantially similar titanium dioxide nanoparticles lacking the carbon modification.

Having generally described this disclosure, a further understanding can be obtained by reference to certain specific examples which are provided herein for purposes of illustration only and are not intended to be limiting unless otherwise specified. The examples below are intended to further illustrate protocols for preparing and characterizing the carbon modified titanium dioxide nanoparticle photocatalysts of the present disclosure. Further, they are intended to illustrate assessing the properties of these materials and assessing their performance in methods for the remediation of aqueous solutions comprising a polychlorinated biphenyl and systems thereof. They are not intended to limit the scope of the claims.

Example 1

Preparation of Catalyst (CM-n-$TiO_2$)

A sonicated sol-gel method was used to fabricate CM-n-$TiO_2$ nanoparticles. Briefly, 10 mL of titanium (IV) isopropoxide as a titanium and carbon containing precursor was slowly added to 10 mL of anhydrous alcohol under ultrasonication. 5 mL of ultrapure Milli-Q water was slowly dripped into the mixture which was subsequently left under sonication for 30 minutes. The was followed by an adjustment of the pH of the solution between 3 and 3.5 using HCl and NaOH, followed by aging at ambient temperature for 24 hours, then filtration, and washing for several times with anhydrous alcohol and ultrapure water. After drying at 80° C. for 12 hours, the powder was calcined at 500° C. for 2 hours in a muffle furnace to form CM-n-$TiO_2$ nanoparticles. For comparison, unmodified n-$TiO_2$ (Loba Chemie Pvt. Ltd, extra pure, India) was used as a reference catalyst.

Example 2

Characterization of Catalyst (CM-n-$TiO_2$)

The X-ray diffraction (XRD) analysis for both photocatalysts was performed using a 6000 X-ray generator (Shimadzu) with a copper K$\alpha$ radiation at 30 mA and 40 kV, at a scan rate of 1.0° $min^{-1}$ over the 2θ range of 20-70°. The UV-vis spectra of both catalysts were recorded on UV-vis Spectrophotometer (Shimadzu, PharmaSpec UV-1700). The morphology of the surface of both photocatalysts was investigated using Field Emission Scanning Electron Microscope (SEM) (JEOL, JSM-7600F, US). Energy Dispersive X-Ray Spectroscopic unit (EDS, X-max 50 $mm^2$, Oxford Instruments) attached to the SEM was used to examine the presence of carbon in both catalysts.

FIG. 1 shows the XRD patterns of both photocatalysts. It is clear to note that the monophase of anatase, is dominant for both nanoparticles. Generally, crystalline anatase is more efficient as a photocatalyst than both rutile and amorphous $TiO_2$ [A. Sclafani, J. M. Herrmann, J. Phys. Chem. 100 (1996) 13655-13661.—incorporated herein by reference in its entirety]. The Scherrer equation was used to calculate the crystal sizes of both photocatalysts, the Scherrer equation is given by formula (I).

$$D = 0.9\lambda/(\beta \cos \theta) \quad (I)$$

In this formula, D represents the mean crystallite size (mm), λ equals the XRD wavelength used (λ=1.54056 Å), β is a full width of the diffraction line observed at half-maximum (FWHM), and θ is the diffraction angle. The crystal sizese of regular and modified catalysts were found to be comparable with values of 41.5 nm and 31.4 nm, respectively. This indicates that the crystal size isn't a controlling element for assessing the performance of both catalysts.

Figure 2:
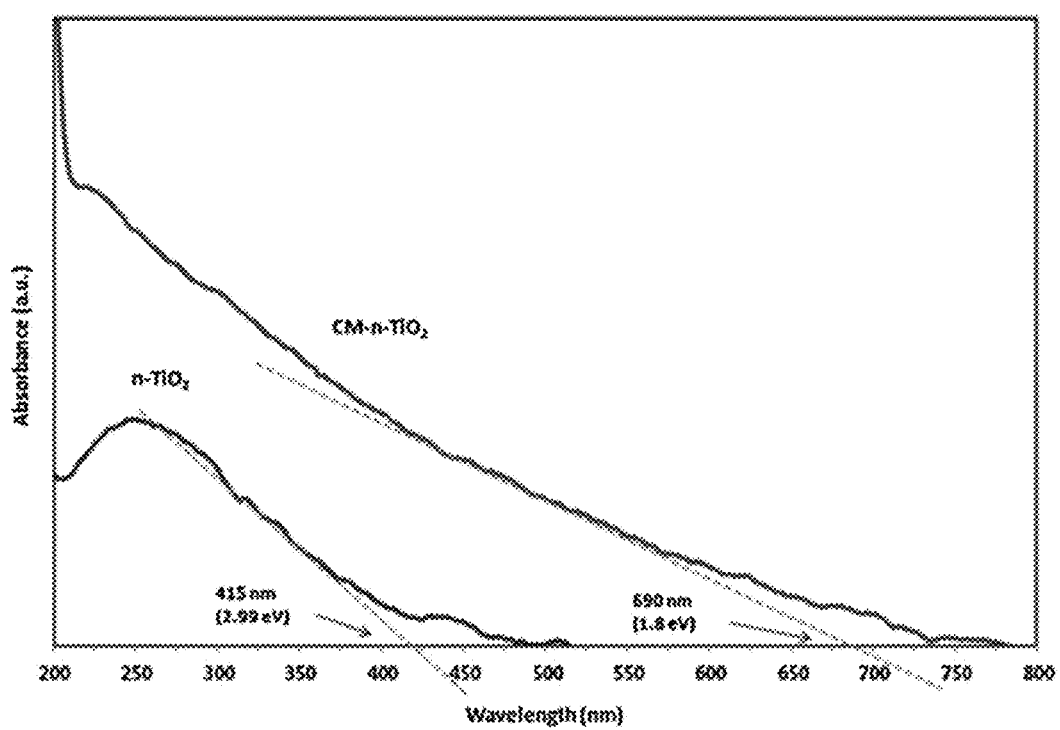
FIG. 2 is an ultraviolet-visible (UV-vis) absorbance spectra of an unmodified titanium dioxide nanoparticle (n-$TiO_2$) photocatalyst and a carbon-modified titanium dioxide nanoparticle (CM-n-$TiO_2$) photocatalyst.

FIG. 2 shows the UV-vis absorbance of carbon modified CM-n-$TiO_2$ and regular unmodified n-$TiO_2$. In comparison with n-$TiO_2$, CM-n-$TiO_2$ exhibits a strong absorption in both ultraviolet and visible regions. This indicates that carbon incorporation enhanced the absorption coefficient of light, $\alpha$, in the UV as well as visible regions for CM-n-$TiO_2$. The may result in a higher photoresponse for CM-n-$TiO_2$ nanoparticles compared to regular unmodified n-$TiO_2$ nanoparticles under light illumination. The intercept of the tangents to the baseline was used to estimate the bandgap (Eg) for each photocatalyst, which were found to be at 415 nm (2.99 eV) for n-$TiO_2$ and at 690 nm (1.8 eV) for CM-n-$TiO_2$. These values were also confirmed by establishing the Tauc plot of transformed Kubelka-Munk function according to formula (II), formula (III), and formula (IV).

$$\alpha h\nu = A(h\nu - E_g)^n \quad (II)$$

$$(F(R)h\nu)^n = A(h\nu - E_g) \quad (III)$$

$$F(R) = \frac{(1-R)^2}{2R} = \frac{\alpha}{S} \quad (IV)$$

Figure 3:
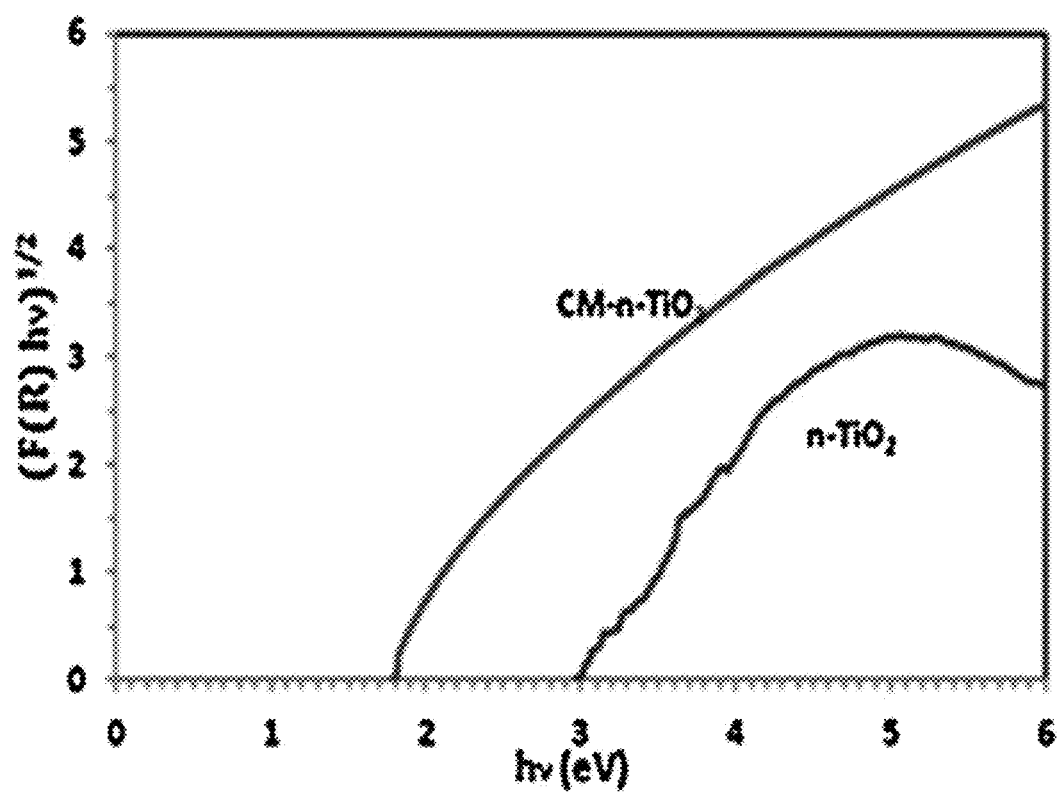
FIG. 3 is a Tauc plot of a transformed Kubelka-Munk function of an unmodified titanium dioxide nanoparticle (n-$TiO_2$) photocatalyst and a carbon-modified titanium dioxide nanoparticle (CM-n-$TiO_2$) photocatalyst.

In this formula, $\alpha$ is the light absorption coefficient, h is Planck's constant, $\upsilon$ is the frequency of vibration, Eg is the bandgap, A is the optical constant, R is the diffused reflectance, n=2 for indirect transitions and ½ for direct transitions, and S is the scattering coefficient [P. Kubelka, J. Opt. Soc. Am. 38 (1948) 448-457; and T. Tauc, R. Grigorovici, A. Vancu, Phys. Status Solidi B 15 (1966) 627-637.—each incorporated herein by reference in its entirety]. FIG. 3 shows the Tauc plot of the transformed Kubelka-Munk function for the two photocatalysts.

The significant reduction of the bandgap value from 2.99 eV to 1.8 eV for CM-n-$TiO_2$, can possibly be explained by the mixing of C 2p with the O 2p valence bands [Y. Nakano, T. Morikawa, T. Ohwaki, Y. Taga, Appl. Phys. Lett. 87 (2005).—incorporated herein in its entirety]. Furthermore, the presence of interstitial and substitutional carbon in C-doped $TiO_2$ was found to be responsible for lowering its bandgap as theoretically explained by Di Valentin et al. [C. Di Valentin, G. Pacchioni, A. Selloni, Chem. Mater. 17 (2005) 6656-6665.—incorporated herein by reference in its entirety]. Generally, the substitutional carbon can narrow the bandgap of $TiO_2$ by forming a new state which lies above the valence band, which in turn enhances the efficiency of the catalyst to absorb visible light [X. Lin, F. Rong, X. Ji, D. Fu, Microporous Mesoporous Mater. 142 (2011) 276-281.—incorporated herein by reference in its entirety].

Figure 4:
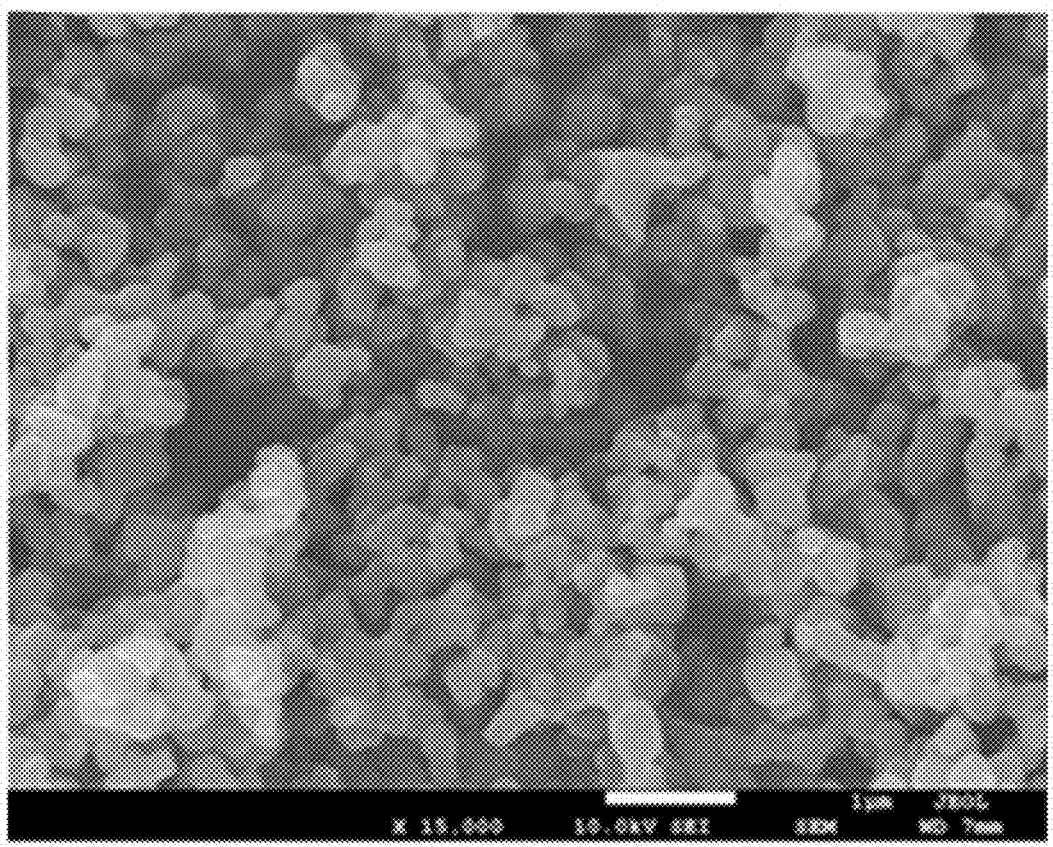
FIG. 4 is a scanning electron microscopy (SEM) image of an unmodified titanium dioxide (n-$TiO_2$) photocatalyst.
Figure 5:
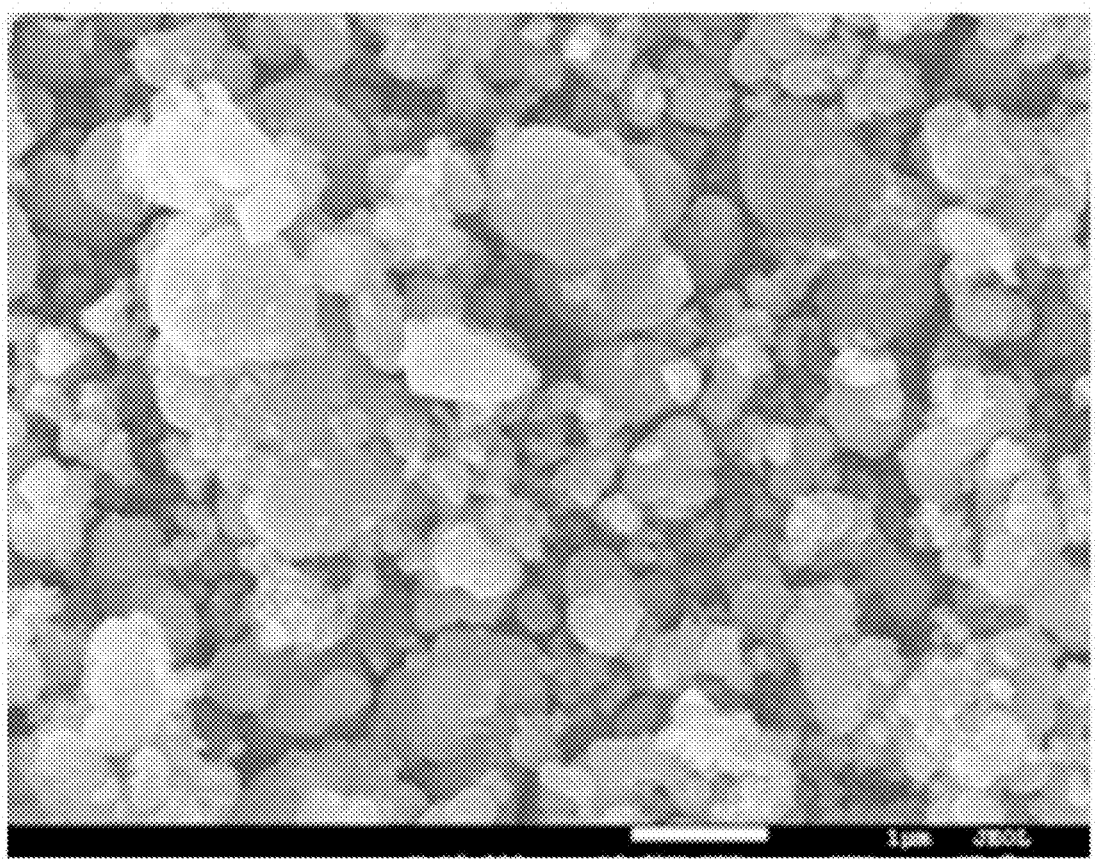
FIG. 5 is a SEM image of a carbon-modified titanium dioxide nanoparticle (CM-n-$TiO_2$) photocatalyst.

FIG. 4 is the SEM image of the unmodified n-$TiO_2$. FIG. 5 is the SEM image of the CM-n-$TiO_2$. The SEM images show the surface morphology of the photocatalysts. The similarity of SEM images is clearly noted. Large quantities of comparable monodispersed small crystals were observed in both samples. EDS analysis confirms the carbon modification of CM-n-$TiO_2$ with 8.98 atomic % carbon, whereas the absence of carbon in n-$TiO_2$ is clearly noted. Table 1 summarizes the optical and chemical properties of each catalyst. As can be seen, the incorporation of carbon (8.98 atomic %) into CM-n-$TiO_2$ lowered the bandgap energy from 2.99 to 1.8 eV. Therefore it is expected that CM-n-$TiO_2$ will have higher photocatalytic activity than n-$TiO_2$ in both UV and visible regions.

TABLE 1

Optical and chemical properties of CM-n-TiO$_2$ and n-TiO$_2$ nanoparticles

| Catalyst | Crystal phase | Crystalline size (nm) | Bandgap (eV) | Atomic % | | |
|---|---|---|---|---|---|---|
| | | | | Ti | O | C |
| CM-n-TiO$_2$ | Anatase | 31.4 | 1.8 | 29.81 | 61.21 | 8.98 |
| n-TiO$_2$ | Anatase | 41.5 | 2.99 | 36.54 | 63.46 | 00.00 |

Example 3

Photocatalytic Removal Experiments in Aqueous Solution at Laboratory Scale

A 500 mL glass reactor was employed as a photoreactor, in which all laboratory scale photodegradation experiments were performed. Both the desired concentration of PCBs (Aroclor 1254 or 1260) and the photocatalyst were loaded inside the photocatalytic reactor and continuously stirred for uniform mixing. Prior to light irradiation, the suspensions were equilibrated for 30 minutes in the dark. Subsequently, the photoreactor was irradiated with a low pressure UV fluorescent lamp (Upland, 15 W of wavelength 365 nm) placed inside a fluorescence cabinet (CC-80, Spectroline).

10 mL of treated PCBs solution was sampled at regular irradiation intervals. The samples containing photocatalyst were centrifuged for 5 minutes and then the supernatant was shaken with 2 mL of a mixture of hexane and dichloromethane (1:1) for 15 minutes. Using a nitrogen evaporator, extracted samples were concentrated to 0.5 mL, then transferred to screw capped vials and stored at 4° C. before analysis. The concentration of PCBs (Ar1254 and Ar1260) was measured using a gas chromatograph coupled with a $^{63}$Ni electron capture detector (GC-ECD, Shimadzu 2010). A Rxi-XLB capillary column (30 m×0.322 mm×0.5 µm) was used. The injection port temperature was held at 250° C. and the detector temperature was kept at 320° C. A constant flow rate of 1.7 mL/min was applied for carrier gas. The volume of 2.0 µL was used for injection. The temperature of the oven was held at 100° C. for 1 minute, ramped to 270° C. at a rate of 30° C./min, and maintained for 1 minute, and finally ramped to 300° C. at a rate of 2.0° C./min and kept for 3 minutes. The removal efficiency (R %) was calculated according to formula (V).

$$R\% = \frac{A_0 - A_t}{A_0} \times 100 \tag{V}$$

In this formula, $A_0$ and $A_t$, are the peak areas of PCBs before (i.e. at zero time) and after irradiation at (t) time, respectively.

Example 4

Figure 6:
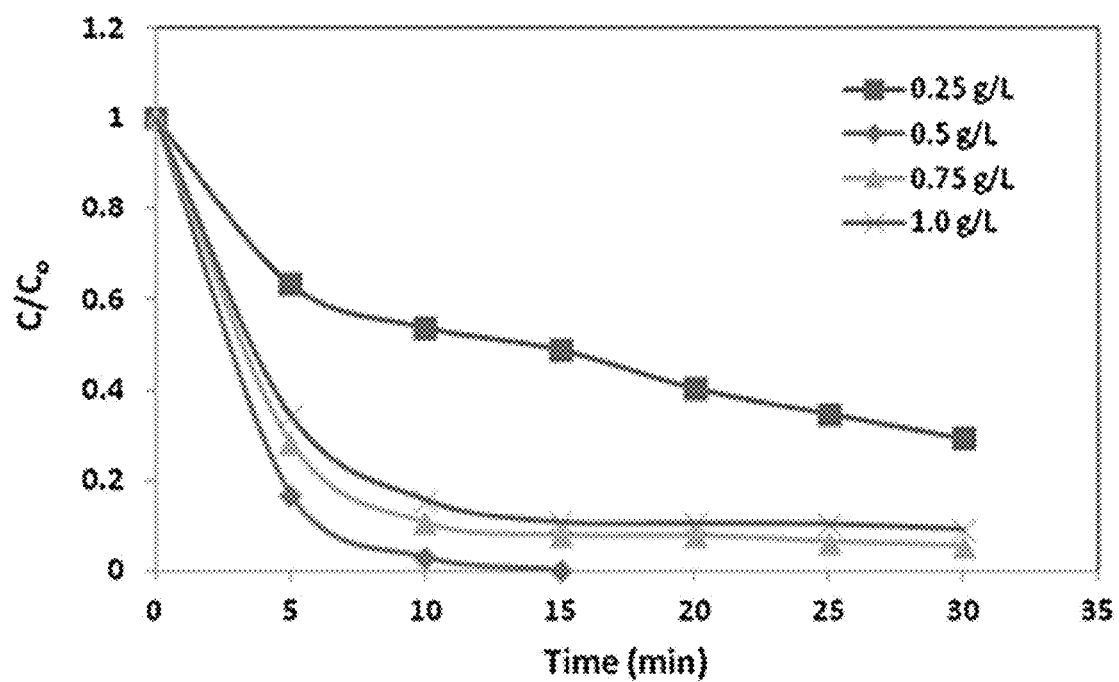
FIG. 6 is a plot of photocatalytic degradation of 1.0 ppm of Aroclor 1254 (Ar 1254) under illumination of light using different dosages of a carbon-modified titanium dioxide nanoparticle (CM-n-$TiO_2$) photocatalyst.
Figure 7:
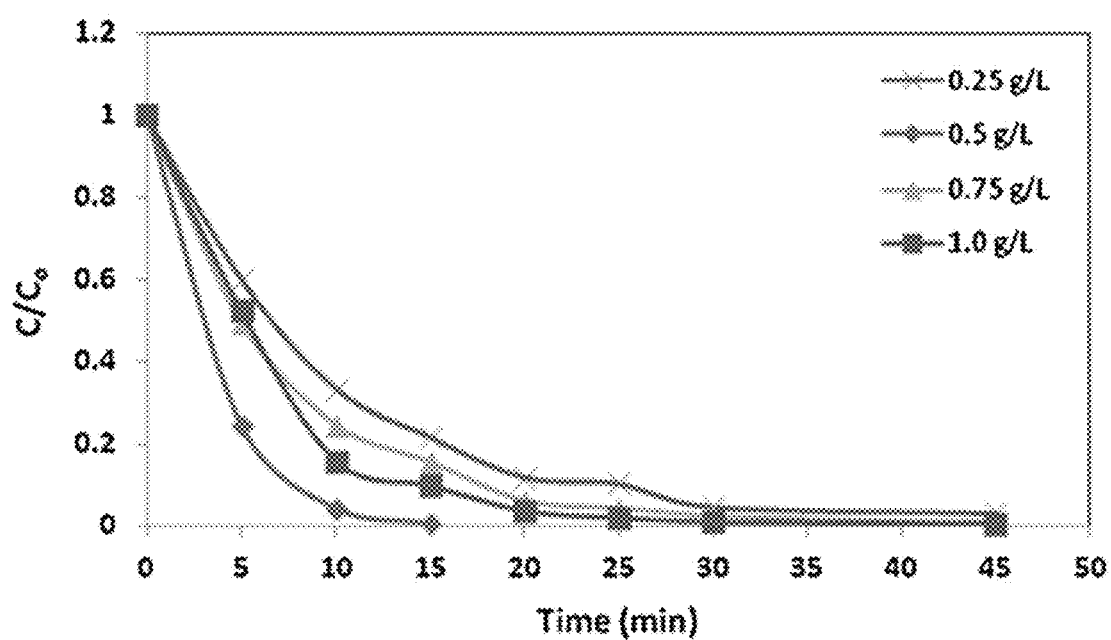
FIG. 7 is a plot of photocatalytic degradation of 1.0 ppm of Aroclor 1260 (Ar 1260) under illumination of light using different dosages of a carbon-modified titanium dioxide nanoparticle (CM-n-$TiO_2$) photocatalyst.

Effects of Catalyst Dose, Solution pH, and Initial Aroclor Concentration in Photocatalytic Removal Experiments in Aqueous Solution at Laboratory Scale First, the catalyst loading was evaluated to guarantee efficient absorption of light photons as well as to avoid any extra dosages of catalyst. FIG. 6 and FIG. 7 show the effect of catalyst dose on photodegradation of 1.0 ppm of each of Ar 1254 (FIG. 6) and Ar 1260 (FIG. 7) under illumination of light. The elevation of catalyst dosage from 0.25 to 0.5 g L$^{-1}$ increases the number of *OH radicals, leading to an enhanced photocatalytic removal rate of Ar 1254 and 1260. A remarkable decrease in the degradation efficiency was clearly noted by the subsequent increasing in the catalyst loading to 0.75 and 1.0 g L$^{-1}$. This can be explained by two factors; the reduction of the number of activated sites on the TiO$_2$ surface due to increased turbidity of the suspension. Additionally, with the overloaded catalyst, particles aggregation increases shadowing effect which in turn reduces the surface area available for light absorption resulting in a reduction of photocatalytic activity [R. Wang, D. Ren, S. Xia, Y. Zhang, J. Zhao, J. Hazard. Mater. 169 (2009) 926-932; and S. Merabet, A. Bouzaza, D. Wolbert, J. Hazard. Mater. 166 (2009) 1244-1249.—each incorporated herein by reference in its entirety]. These results reveal that, the value of 0.5 g L$^{-1}$ is an advantageous CM-n-TiO$_2$ dosage for efficient photocatalytic degradation of the examined concentration of PCBs.

Generally, the pH of the solution influences the transfer of the interfacial electrons and the photo-redox mechanism for photocatalytic degradation reactions by affecting the charge of the semiconductor surface [M. C. Lu, G. D. Roam, J. N. Chen, C. P. Huang, J. Photochem. Photobiol. A: Chem.76 (1993) 103-109.—incorporated herein by reference in its entirety]. In aqueous solution, there are three possible functional groups that can exist on the TiO$_2$ surface: TiOH$^2$, TiOH, and TiO$^-$. The presence of any of these groups is determined by the zero point of charge (pH$_{pzc}$) of TiO$_2$. When pH is greater than pH$_{pzc}$ (formula (VI), a negatively charged TiO$_2$ surface, with the species TiO$^-$ exists, whereas, at pH less than pH$_{pzc}$ (formula (VII)), a positively charged group (TiOH$^{2+}$) is formed on the TiO$_2$ surface. These relationships are shown in formula (VI) and formula (VII).

$$\text{TiOH} + \text{OH}^- \rightarrow \text{TiO}^- + \text{H}_2\text{O} \tag{VI}$$

$$\text{TiOH} + \text{H}^+ \rightarrow \text{TiOH}_2^+ \tag{VII}$$

Figure 8:
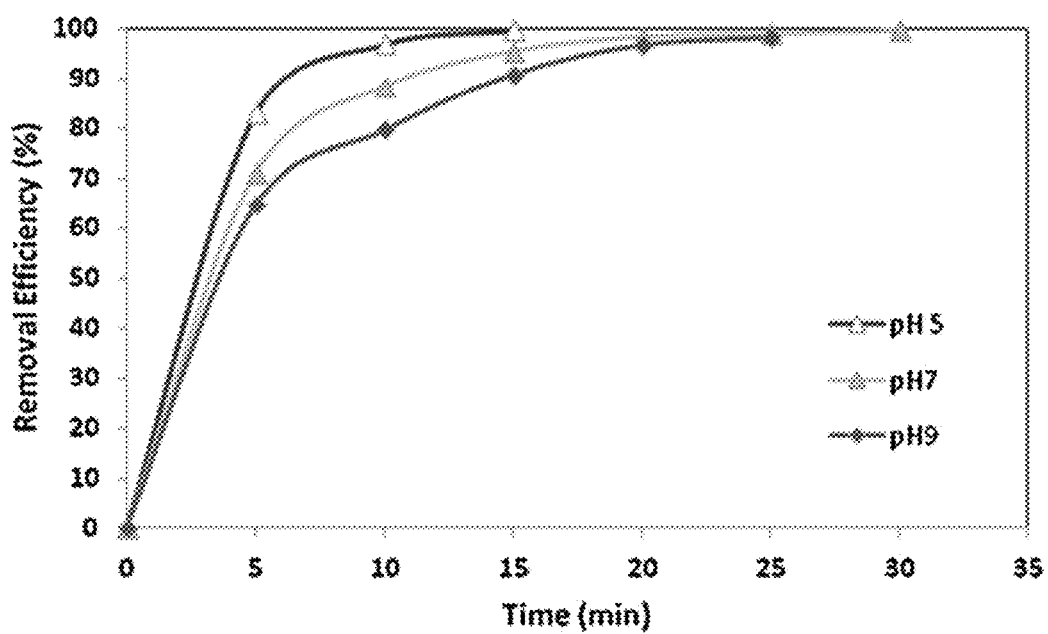
FIG. 8 is a plot illustrating the effect of solution pH on the photocatalytic degradation of 1.0 ppm Aroclor 1254 (Ar 1254) under illumination of light using a carbon-modified titanium dioxide nanoparticle (CM-n-$TiO_2$) photocatalyst dosage of 0.5 g $L^{-1}$.
Figure 9:
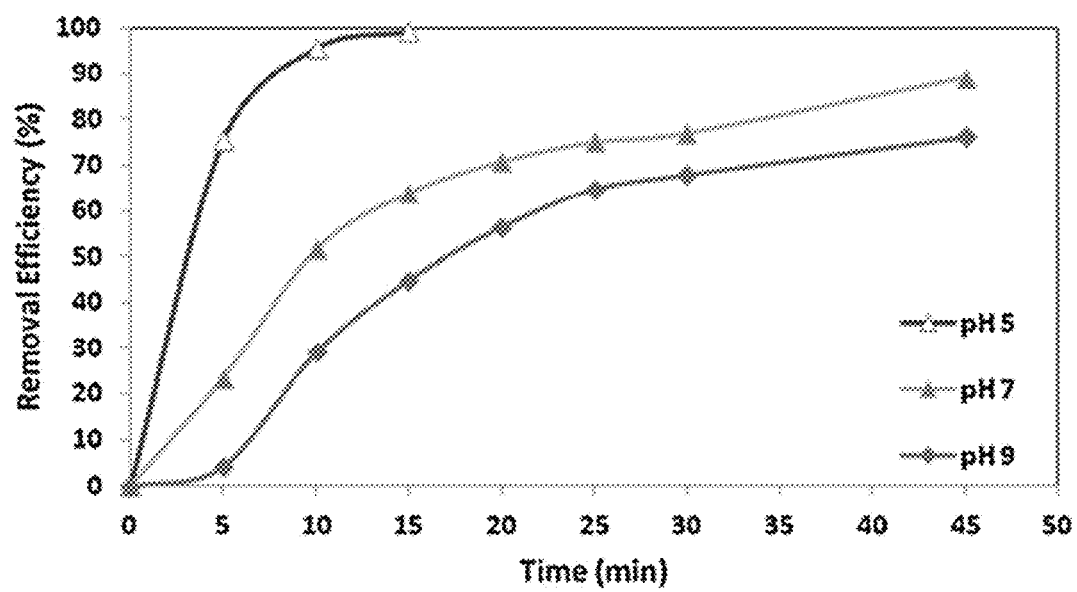
FIG. 9 is a plot illustrating the effect of solution pH on the photocatalytic degradation of 1.0 ppm Aroclor 1260 (Ar 1260) under illumination of light using a carbon-modified titanium dioxide nanoparticle (CM-n-$TiO_2$) photocatalyst dosage of 0.5 g $L^{-1}$.

The effect of pH on the degradation of Aroclor 1254 and 1260 was investigated by changing the pH value of PCBs solution from 5 to 9, while all other experimental parameters were maintained constant. FIG. 8 and FIG. 9 show the effect of pH on photocatalytic degradation of 1.0 ppm of each of Ar 1.254 (FIG. 8) and Ar 1260 (FIG. 9) under illumination of light. As can be observed, the efficiency of CM-n-TiO$_2$ toward the degradation of Ar 1254 (FIG. 8) and Ar 1260 (FIG. 9) decreases with the increase in pH from 5 to 9, indicating an advantageous value of pH 5. These results are consistent with those reported by Wong et al. where the photodegradation of 2,2',3,3'-tetrachlorobiphenyl was favorable in acidic (pH 5.5) rather than in alkaline medium [K. H. Wong, S. Taob, R. Dawsonb, P. K. Wong, J. Hazard. Mater: B109 (2004)149-155.—incorporated herein by reference in its entirety].

Figure 10:
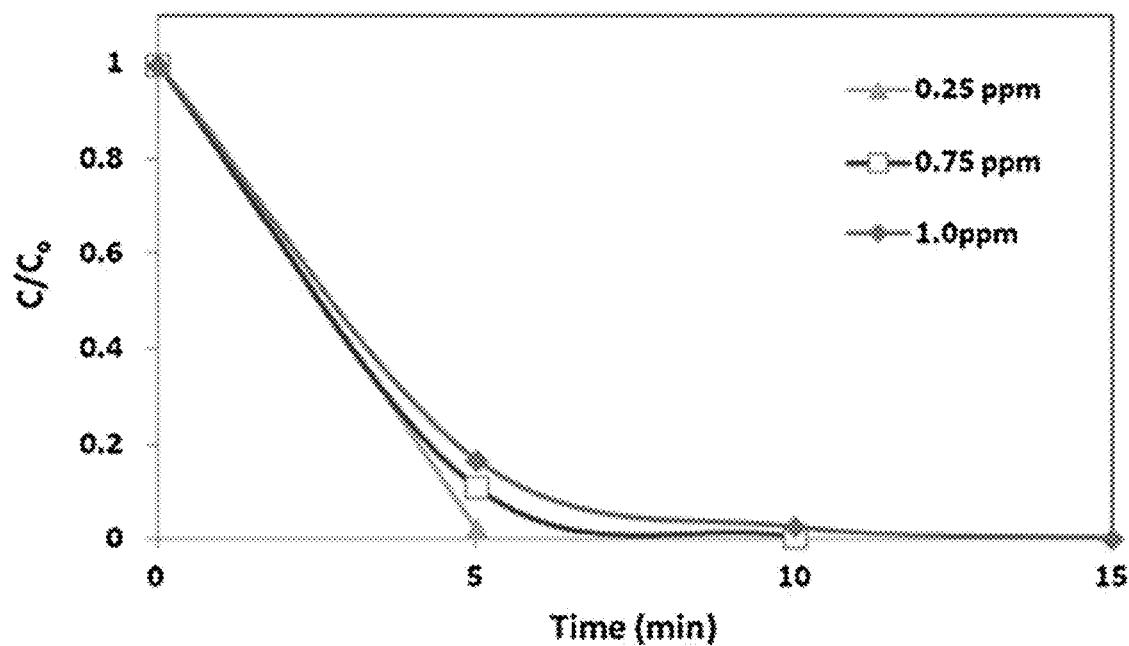
FIG. 10 is a plot illustrating the effect of the initial concentration of Aroclor 1254 (Ar 1254) on its photodegradation rate at pH 5 under illumination of light using a carbon-modified titanium dioxide nanoparticle (CM-n-$TiO_2$) photocatalyst dosage of 0.5 g $L^{-1}$.
Figure 11:
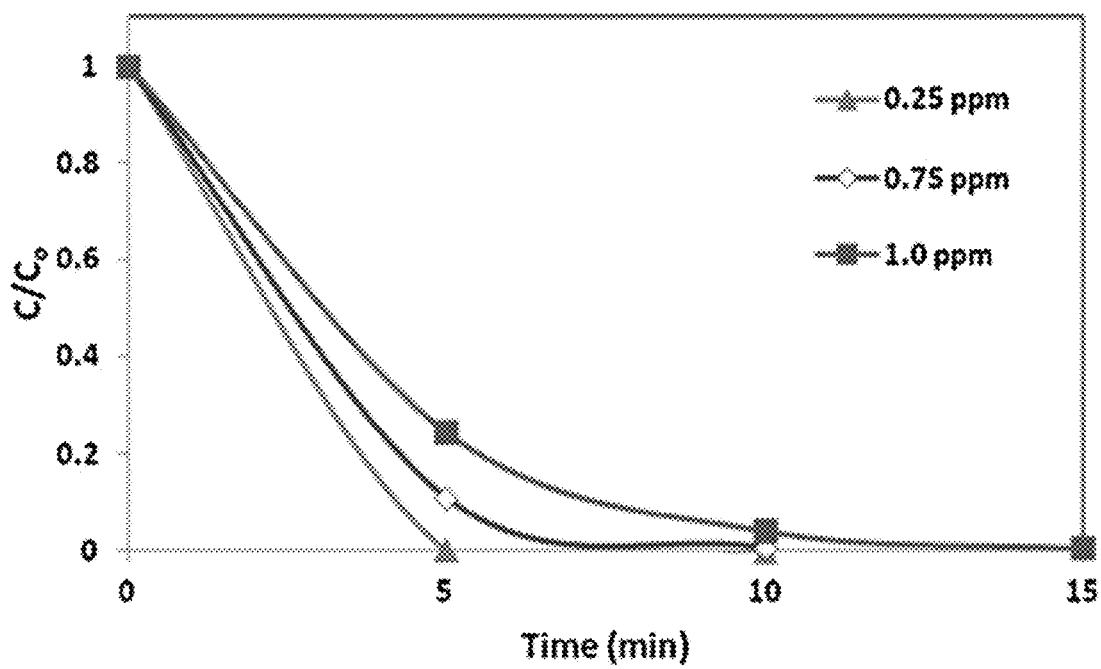
FIG. 11 is a plot illustrating the effect of the initial concentration of Aroclor 1260 (Ar 1260) on its photodegradation rate at pH 5 under illumination of light using a carbon-modified titanium dioxide nanoparticle (CM-n-$TiO_2$) photocatalyst dosage of 0.5 g $L^{-1}$.

The effect of the initial Aroclor (1254 and 1260) concentrations (0.25-1.0) ppm) on their photocatalytic degradation rate was studied at the most favorable conditions of 0.5 g L$^{-1}$ of CM-n-TiO$_2$ and pH 5. FIG. 10 and FIG. 11 show the effect of the initial concentration of Ar 1254 (FIG. 10) and Ar 1260 (FIG. 11) on their photodegradation rate. It is clear, the photocatalytic removal efficiency was remarkably influenced by the initial concentration of Aroclor. As the initial Aroclor concentration increased, the illumination time needed for complete elimination of Aroclor was extended. The reduction of the removal efficiency can be explained by the fact that, as initial concentration increases, more Aroclor molecules are adsorbed on the surface of the photocatalyst, so that less amount of *OH radicals are generated as less amount of photons are capable of reaching the catalyst surface [K. M. Parida, S. S. Dash, D. P. Das, J. Colloid Interface Sci. 298 (2006) 787-793.—incorporated herein by reference in its entirety]. Several studies have reported that higher concentrations of organics deactivate the active sites of the photocatalyst by inducing the generation of reaction intermediates that could occupy its surface [S. Ahmed, M. G. Rasul, W. N. Martens, R. Brown, M. A. Hashib, Desalination 261(2010) 3-18.—incorporated herein by reference in its entirety].

Example 5

Kinetic Studies of Photocatalytic Removal Experiments in Aqueous Solution at Laboratory Scale The model most commonly employed to depict the kinetics of photocatalytic reactions of aqueous organics is the model proposed by the Langmuir-Hinshelwood (L-H) [A. V. Petukhov, Chem. Phys. Lett. 277 (1997) 539-544; and B. Bayarri, J. Gimenez, D. Curco, S. Esplugas, Catal. Today 101 (2005) 227-236; and Er. Kusvuran, A. Samil, O. M. Atanur, O. Erbatur, Appl. Catal. B: Environ. 58(2005) 211-216.—each incorporated herein by reference in its entirety]. According to this model, the relationship between the degradation rate (r) and concentration of the reactant in water at time t(C), can be expressed by formula (VIII).

$$r = -\frac{dc}{dt} = \frac{k_r K_{ad}}{1 + K_{ad} C} \quad \text{(VIII)}$$

In this formula, the constants $k_r$ and $K_{ad}$ represent the rate and the adsorption equilibrium. This equation can be simplified to represent the pseudo-first order reaction when $C_0$ is very small by formula (IX).

$$\ln\left(\frac{C_0}{C}\right) = k_r k_{ad} t = k_{app} t \quad \text{(XI)}$$

Figure 12:
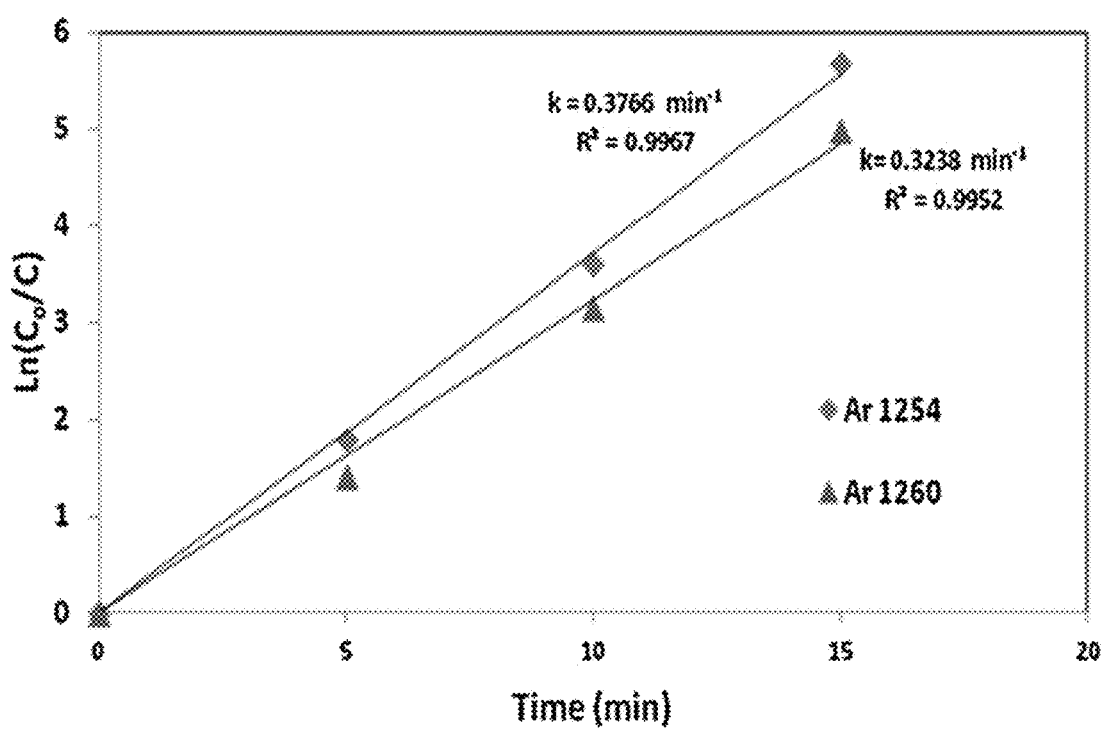
FIG. 12 is a kinetic analysis plot of the photocatalytic degradation of Aroclor 1254 (Ar 1254) and Aroclor 1260 (Ar 1260) at pH 5 under illumination of light using a carbon-modified titanium dioxide nanoparticle (CM-n-$TiO_2$) photocatalyst dosage of 0.5 g $L^{-1}$.

In this formula, $k_{app}$ and $C_0$ are the apparent first-order rate constant and the concentration at zero time, respectively. By plotting ln ($C_0$/C) versus irradiation time (t) a linear behavior that indicates a pseudo-first order kinetics for the photocatalytic degradation of PCBs was obtained. FIG. 12 shows this plot.

Example 6

Figure 13:
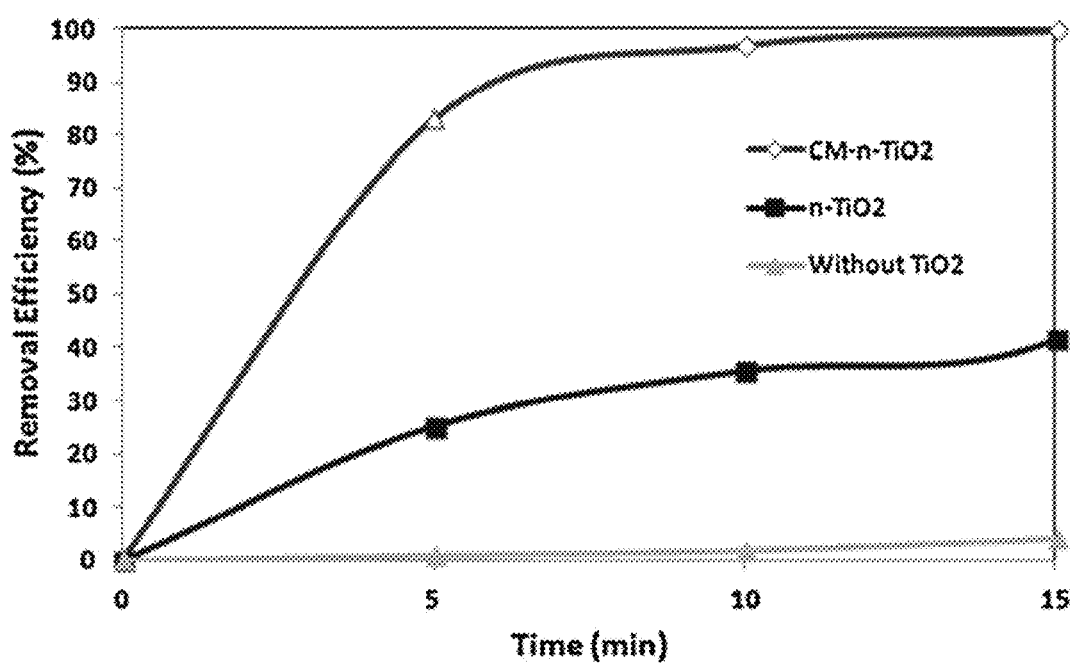
FIG. 13 is a comparative plot of photocatalytic degradation of Aroclor 1254 (Ar 1254) at pH 5 under illumination of light using an unmodified titanium dioxide nanoparticle (n-$TiO_2$) photocatalyst dosage of 0.5 g $L^{-1}$ compared to a carbon-modified titanium dioxide nanoparticle (CM-n-$TiO_2$) photocatalyst dosage of 0.5 g $L^{-1}$.
Figure 14:
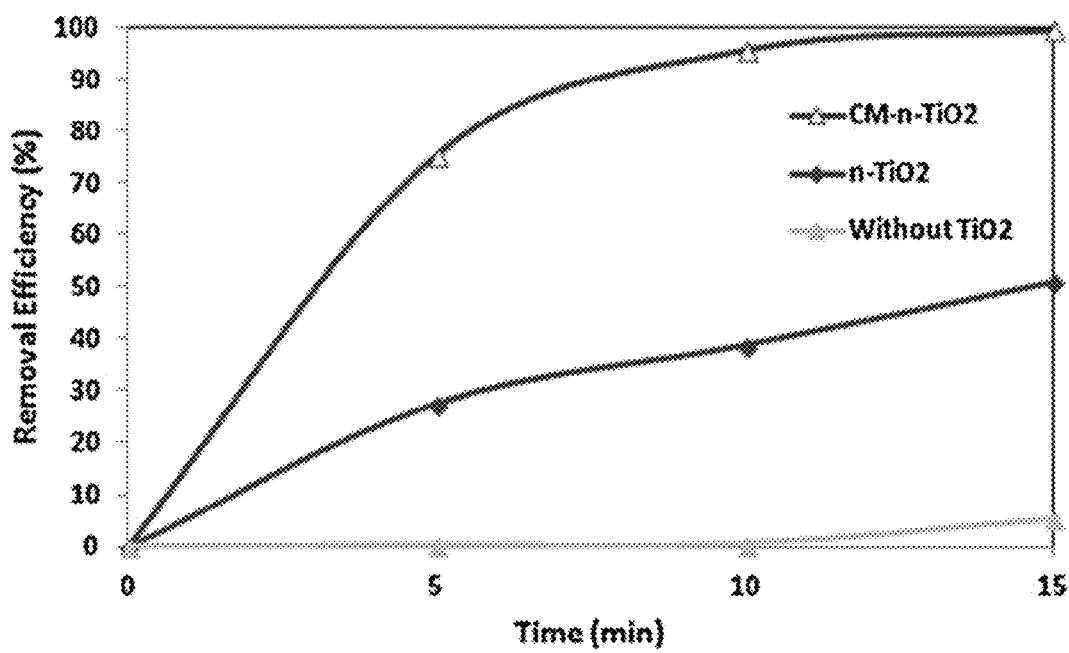
FIG. 14 is a comparative plot of photocatalytic degradation of Aroclor 1260 (Ar 1260) at pH 5 under illumination of light using an unmodified titanium dioxide nanoparticle (n-$TiO_2$) photocatalyst dosage of 0.5 g $L^{-1}$ compared to a carbon-modified titanium dioxide nanoparticle (CM-n-$TiO_2$) photocatalyst dosage of 0.5 g $L^{-1}$.

Comparative Photocatalytic Performance of the Photocatalysts in Aqueous Solution at Laboratory Scale The photocatalytic performance of CM-n-TiO$_2$ was comparatively evaluated with regular n-TiO$_2$ under identical conditions. FIG. 13 and FIG. 14 illustrate the photodegradation of Ar 1254 (FIG. 13) and Ar 1260 (FIG. 14) at pH 5 and 0.5 g L$^{-1}$ of the photocatalysts n-TiO$_2$ and CM-n-TiO$_2$. It is observed that no significant degradation was obtained under the photolysis conditions (under light illumination only and in the absence of the photocatalyst). Using CM-n-TiO$_2$, only 15 minutes of irradiation was required to complete removal of Ar 1254 (FIG. 13) and Ar 1260 (FIG. 14). Whereas using the same dose of n-TiO$_2$, the removal efficiencies of Ar 1254 and Ar 1260 were declined to 41.6% and 50.8%, respectively. This improved photoactivity of CM-n-TiO$_2$ nanoparticles is due to carbon incorporation, which helped in a remarkable enhancement in its absorption coefficient, α, of light in the UV region and also due to a reduction of its bandgap.

Example 7

Photocatalytic Removal Experiments in Seawater at Laboratory Scale and at Pilot-Plant Scale Clean seawater samples, collected from Sharm Obhur, Jeddah Red Sea coast, were spiked with various concentrations of PCBs (Aroclor 1254 and Aroclor 1260). Photocatalytice degradation experiments were performed at laboratory level with UV light and at pilot-plant scale with natural solar radiation. The effects of operating parameters including CM-n-TiO$_2$ loading and pH of the solution on the photodegradation rate of PCBs were investigated first at lab scale to reach advantageous conditions and then were applied at pilot-plant scale.

For lab scale photocatalytic experiments, a 500 mL Pyrex glass reactor was used as a batch reactor under illumination of UV light. Both contaminated samples and the photocatalyst were loaded inside the photocatalytic reactor and continuously stirred for uniform mixing. Prior to light irradiation, the suspensions were equilibrated for 30 minutes in the dark. Subsequently, the photoreactor was irradiated with a low pressure UV fluorescent lamp (Upland, 15 W of wavelength 365 nm) and placed inside a fluorescence cabinet (CC-80, Spectroline).

A solar pilot-plant scale reactor, or Solar Falling Film Reactor (SFFR), was designed and built. The performance of the CM-n-TiO$_2$/SFFR system was evaluated towards the photocatalytic removal of PCBs under real sunlight illumination. The SFFR consists of a flat tray, a top distributor, a bottom collector, a pump (Pedrollo, Itally, model: PKm 60-BR, 550 W), and a batch tank (equipped with electric mixer to allow homogenization) located underneath the flat tray. The flat tray, top distributor, and bottom collector are made of stainless steel, Grade 316, to avoid rust problems that may affect the measurements. The flat tray is about 1.0 m wide by 1.5 m length with 10 cm side height. The fluid flows from the tank using the pump to the top distributor of the SFFR down to the flat tray to the bottom collector and back to the tank again; the water thus continuously circulates in a closed circuit. The flow rate is adjusted by a by-pass valve. The flat tray is mounted on a stainless steel stand with pivot allowing accurate adjustment of the tilt angle; the tilt angle was adjusted to be 22°±10° for maximum solar collection in Jeddah. The SFFR has an irradiated surface of 1.5 m$^2$ and total volume of 20 L. The experiments were carried out on sunny days between 11:00 a.m. and 3:00 p.m. The average solar intensity was 1140 Wm$^{-2}$, measured by a Field Scout Light Sensor Radar (Spectrum Technologies, Inc.) equipped with a 3670i Silicon Pyranometer Sensor.

Treated PCBs solution was sampled at regular irradiation intervals. The samples containing photocatalyst were centrifuged for 5 minutes and then the supernatant was shaken with 2 mL of a mixture of hexane and dichloromethane (1:1) for 15 minutes. Using a nitrogen evaporator, extracted samples were concentrated to 0.5 mL and then transferred to screw capped vials and stored at 4° C. for before analysis. The concentration of PCBs (Ar 1254 and Ar 1260) was measured using a gas chromatograph coupled with $^{63}$Ni electron capture detector (GC-ECD, Shimadzu 2010). Rxi-XLB capillary column (30 m×0.32 mm×0.5 μm) was used. The injection port temperature was held at 250° C. and the detector temperature was kept at 320° C. A constant flow rate of 1.7 mL/min was applied for carrier gas. The volume of 2.0 μL was used for injection. The temperature of the oven was held at 100° C. for 1 minute, ramped up to 270° C. at a rate of 30° C./min, and maintained for 1 minute and finally ramped up to 300° C. at a rate of 2.0° C./min and kept for 3 minutes. The PCBs were identified by comparison of retention time using a series of PCBs standards. The removal efficiency (R %) was calculated according to formula (V).

$$R\% = \frac{A_0 - A_t}{A_0} \times 100 \quad \text{(V)}$$

In this formula, $A_0$ and $A_t$ are the peak areas of PCBs before (i.e. at zero time) and after irradiation at (t) time, respectively.

Example 8

Figure 15:
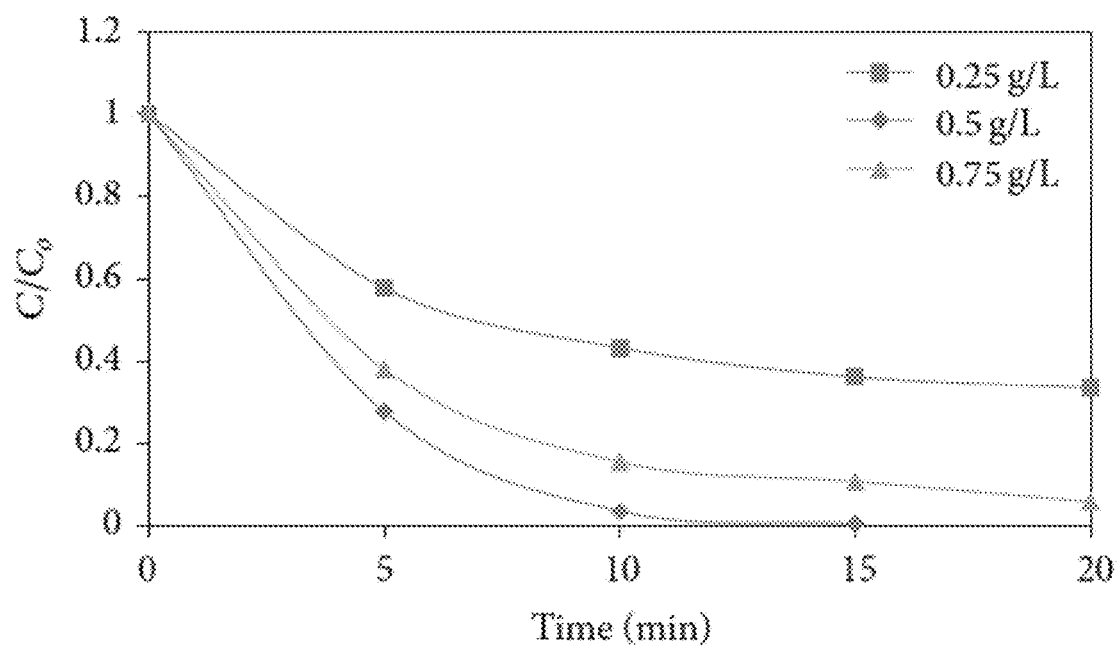
FIG. 15 is a plot of photocatalytic degradation of a mixture of Ar 1254 (0.5 ppm) and Ar 1260 (0.5 ppm) in seawater under illumination of UV light using different dosages of a carbon-modified titanium dioxide nanoparticle (CM-n-$TiO_2$) photocatalyst.

Effects of Catalyst Dose and Solution pH in Photocatalytic Degradation Experiments in Seawater at Laboratory Scale The effect of $CM$-$n$-$TiO_2$ dose on the photocatalytic degradation of a mixture of Ar 1254 (0.5 ppm) and Ar 1260 (0.5 ppm) in seawater under illumination of UV light was studied to attain an advantageous catalyst loading. FIG. 15 shows the effect of catalyst dose on the photocatalytic degradation. It was noted that the increase in the amount of catalyst from 0.25 g $L^{-1}$ to 0.5 g $L^{-1}$ increases the photocatalytic degradation rate due to the increase of the number of hydroxyl radicals. Further increase in the catalyst loading leads to the reduction of the degradation rate, revealing an advantageous catalyst loading of 0.5 g/L. The observed decrease in degradation rate can be attributed to the agglomeration of catalyst particles in addition to the shading by suspension.

Figure 16:
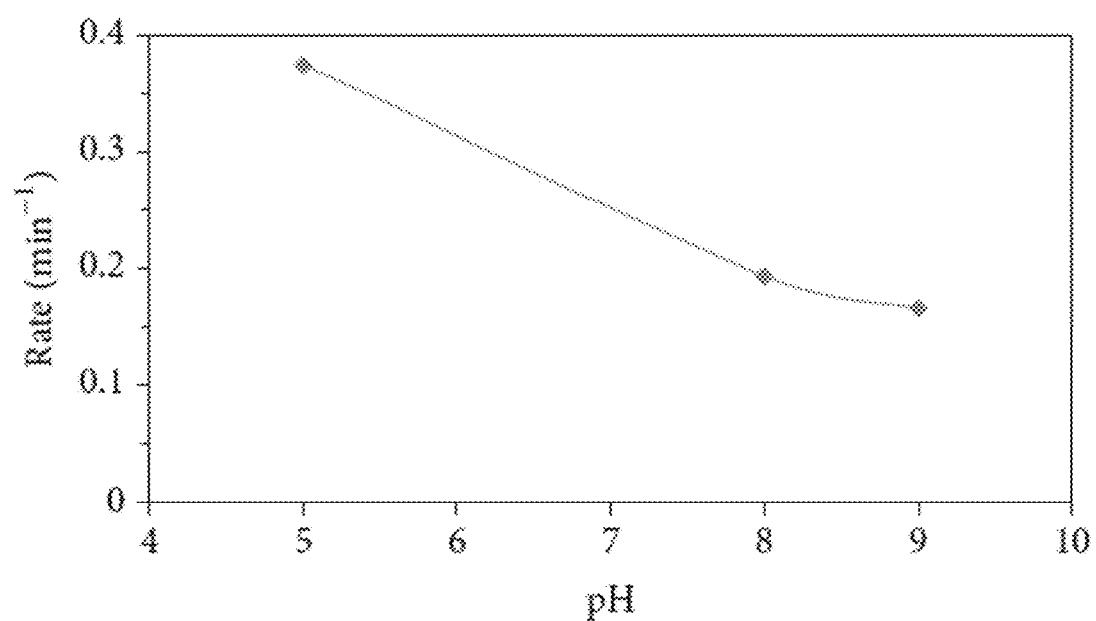
FIG. 16 is a plot illustrating the effect of pH on the photocatalytic degradation of a mixture of Ar 1254 (0.5 ppm) and Ar 1260 (0.5 ppm) in seawater under illumination of UV light using 0.5 g $L^{-1}$ of a carbon-modified titanium dioxide nanoparticle (CM-n-$TiO_2$) photocatalyst.

The effect of pH on the photodegradation of PCBs in seawater under illumination of UV light using $CM$-$n$-$TiO_2$ was studied at three different pH values 5, 7, and 9. FIG. 16 shows the effect of pH on the photocatalytic degradation. It is clearly shown that rate of the photodegradation process of PCBs is dependent on the pH values. When the pH value is 5, a rapid degradation process for PCBs with the highest degradation rate (0.3742 $min^{-1}$) was obtained. This value is 2.26 times higher than that obtained at pH 9. Generally, the mechanism of the photocatalytic degradation reaction using $TiO_2$ as a photocatalyst depends on the adsorption between the target compound and the photocatalyst. The extent of such adsorption depends on the charge of the degraded compound as well as the catalyst, which in turn depends on the pH of a given solution. At pH values lower than the point of zero charge ($pH_{pzc}$) of $TiO_2$, a positively charged $TiO_2$ surface with the species $TiOH_2^+$ exists, while the PCBs and intermediates are negatively charged naturally. Consequently, the adsorption of PCBs is favorable at low pH due to the electrostatic attraction. Furthermore, formation of carbonate ions, which are effective scavengers of the hydroxyl radical (*OH), is favorable at high pH values; as a result, reduction of the degradation efficiency was observed.

Example 9

Figure 17:
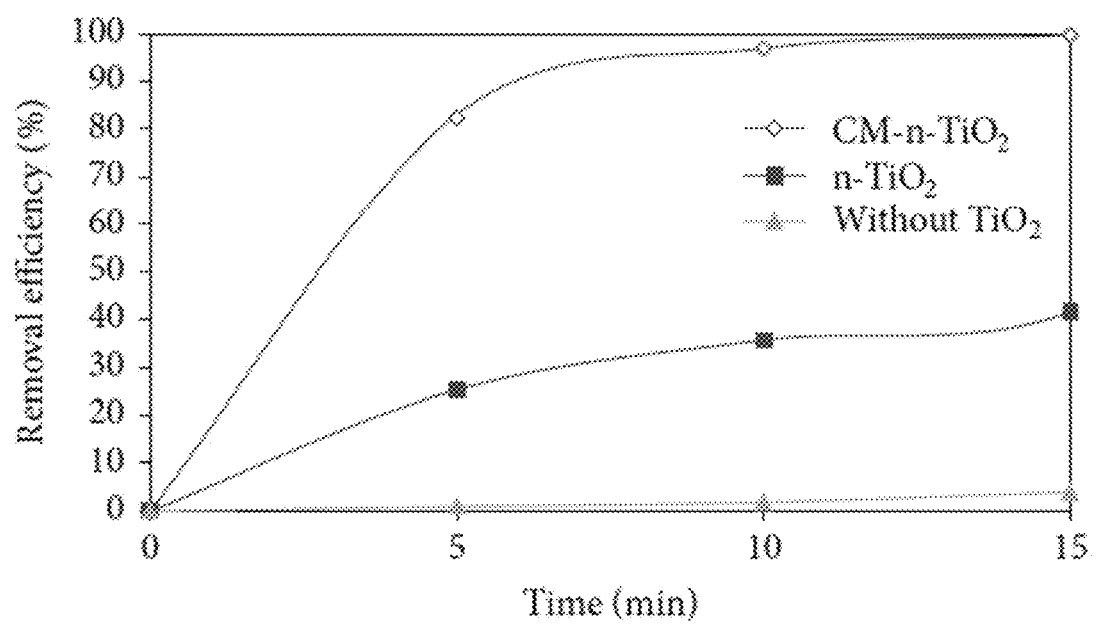
FIG. 17 is a comparative plot of photocatalytic degradation of a mixture of Ar 1254 (0.5 ppm) and Ar 1260 (0.5 ppm) in seawater under illumination of UV light using an unmodified titanium dioxide nanoparticle (n-$TiO_2$) photocatalyst compared to a carbon-modified titanium dioxide nanoparticle (CM-n-$TiO_2$) photocatalyst.

Comparative Photocatalytic Performance of the Photocatalysts in Seawater at Laboratory Scale In order to examine the photocatalytic efficiency in seawater of $CM$-$n$-$TiO_2$, comparison with unmodified $n$-$TiO_2$ was performed under the same advantageous experimental conditions. FIG. 17 illustrates the photodegradation of a mixture of Ar 1254 (0.5 ppm) and Ar 1260 (0.5 ppm) in seawater of the photocatalysts $n$-$TiO_2$ and $CM$-$n$-$TiO_2$. The photocatalytic efficiency of $CM$-$n$-$TiO_2$ (0.5 g $L^{-1}$) towards the photocatalytic degradation of a mixture of Ar 1254 (0.5 ppm) and Ar 1260 (0.5 ppm) in seawater at the advantageous pH 5 under illumination of UV light is much higher than that of $n$-$TiO_2$. Complete degradation of PCBs was achieved after 15 minutes of UV light illumination. In contrast, when the reference $TiO_2$ was used, only 45.92% of the same concentration of PCBs was removed after the same irradiation period. The remarkable enhancement in the photocatalytic activity of $CM$-$n$-$TiO_2$ nanoparticles can be attributed to the narrowing of the optical bandgap energy from 2.99 eV for $n$-$TiO_2$ to 1.8 eV for $CM$-$n$-$TiO_2$ as a result of the carbon modification of $TiO_2$. The significant narrowing of the optical bandgap energy of $CM$-$n$-$TiO_2$ can be ascribed to the mixing of C 2p with the O 2p valence bands as a result of the carbon modification of titanium oxide. The observed optical behavior of the low bandgap energy for the synthesized $CM$-$n$-$TiO_2$ is in good agreement with the previously reported $E_g$ values of 2.35 eV, 1.45 eV, and 1.86 eV. Furthermore, theoretical studies by Di Valentin et al. addressed the notion that the presence of interstitial and substitutional carbon dopants incorporated into $TiO_2$ drastically lowered its bandgap. Nie and Sohlberg obtained a low bandgap value of 2.32 eV by incorporation of carbon into $n$-$TiO_2$ and predicted the possibility of achieving a low bandgap of 1.58 eV by some complex carbon incorporation [X. Nie and K. Sohlberg, "The influence of surface reconstruction and C-impurities on photocatalytic water dissociation by TiO2," in *Materials Research Society Symposium Proceedings on Materials and Technology for Hydrogen Economy*, G.-A. Nazri et al., Ed., vol. 801 of *MRS Proceedings*, p. 205, Boston, Mass., USA, December 2003.—incorporated herein by reference in its entirety].

Example 10

Photocatalytic Degradation in Seawater at Pilot-Plant Scale

Figure 18:
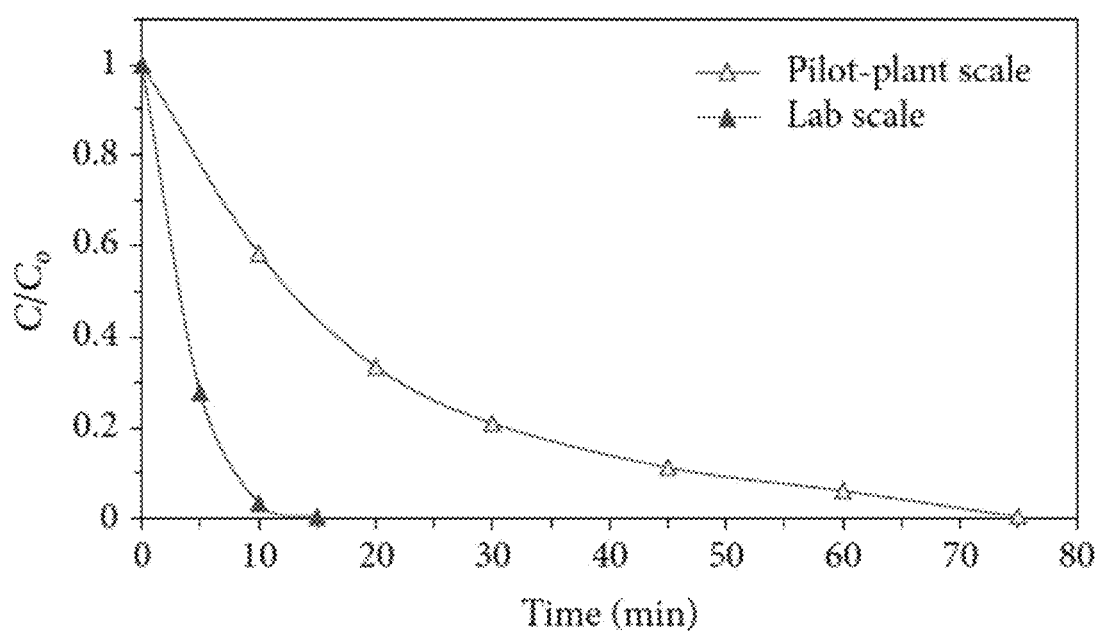
FIG. 18 is a comparative plot of photocatalytic degradation of polychlorinated biphenyls (PCBs) in seawater using a carbon-modified titanium dioxide nanoparticle (CM-n-$TiO_2$) photocatalyst under illumination UV light at lab scale compared to under illumination of natural sunlight at pilot plant scale.

To evaluate the viability and the performance of the solar pilot plant (SFFR), the photocatalytic degradation of PCBs (1.0 ppm) in seawater was examined at the advantageous conditions, obtained from laboratory scale experiments, of pH 5 and 0.5 g $L^{-1}$ of $CM$-$n$-$TiO_2$. FIG. 18 shows the photocatalytic degradation of PCBs (1.0 ppm) in seawater using $CM$-$n$-$TiO_2$ at lab scale and pilot-plant scale. Complete degradation of PCBs was achieved after 15 and 75 minutes of irradiation under UV (lab scale) and sunlight (pilot plant), respectively. It is noted that the remediation of PCBs at lab scale under UV light for a 500 mL sample was successfully extrapolated to a larger pilot-plant system for 20 L of polluted seawater under illumination of real sunlight.

Figure 19:
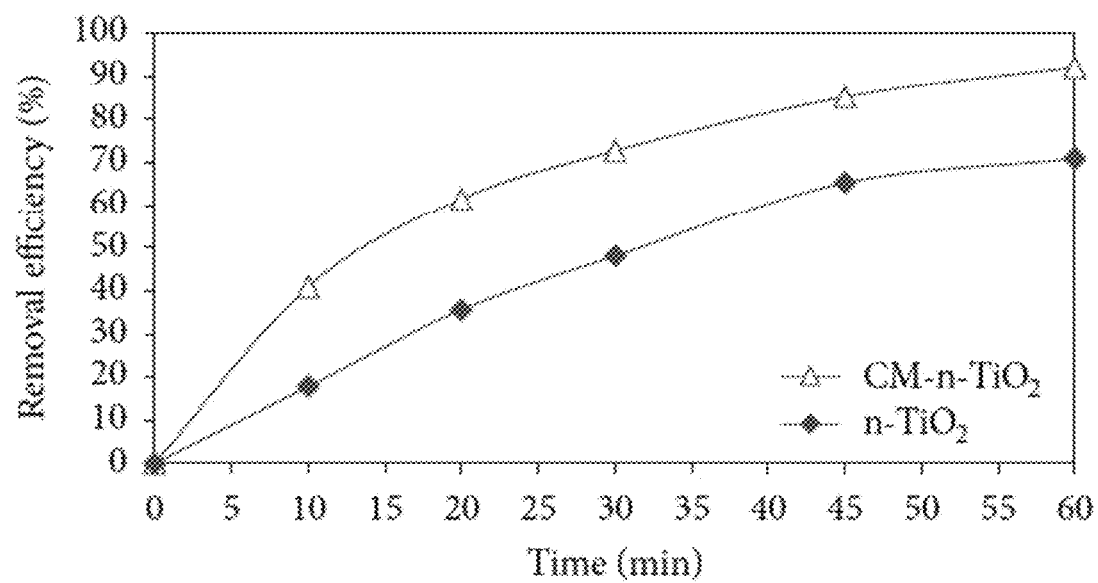
FIG. 19 is a comparative plot of photocatalytic degradation of 0.5 ppm Aroclor 1254 (Ar 1254) in seawater at pH 5 under illumination of natural sunlight at pilot plant scale using an unmodified titanium dioxide nanoparticle (n-$TiO_2$) photocatalyst dosage of 0.5 g $L^{-1}$ compared to a carbon-modified titanium dioxide nanoparticle (CM-n-$TiO_2$) photocatalyst dosage of 0.5 g $L^{-1}$.
Figure 20:
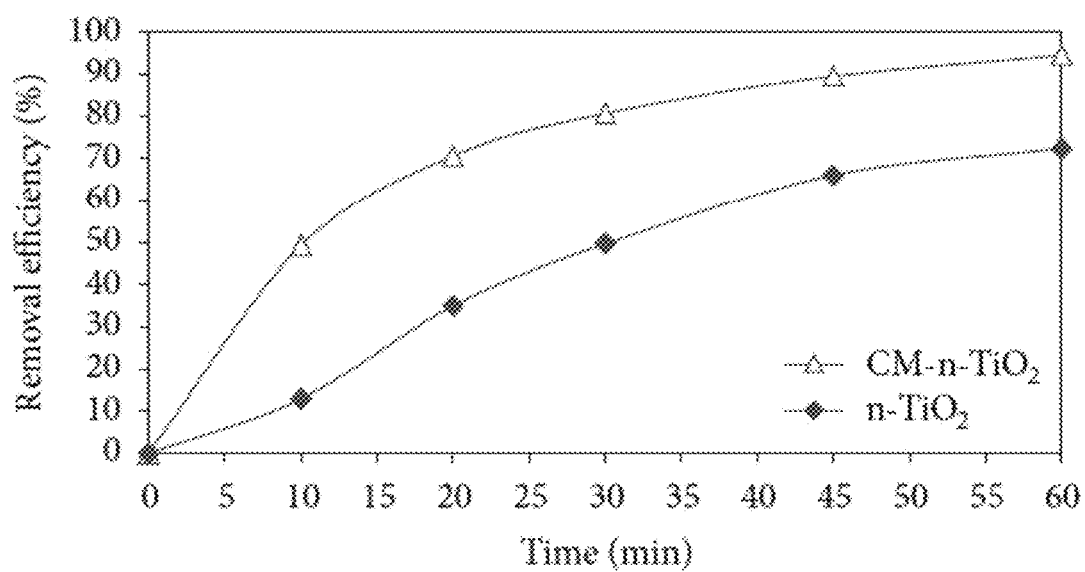
FIG. 20 is a comparative plot of photocatalytic degradation of 0.5 ppm Aroclor 1260 (Ar 1260) in seawater at pH 5 under illumination of natural sunlight at pilot plant scale using an unmodified titanium dioxide nanoparticle (n-$TiO_2$) photocatalyst dosage of 0.5 g $L^{-1}$ compared to a carbon-modified titanium dioxide nanoparticle (CM-n-$TiO_2$) photocatalyst dosage of 0.5 g $L^{-1}$.
Figure 21:
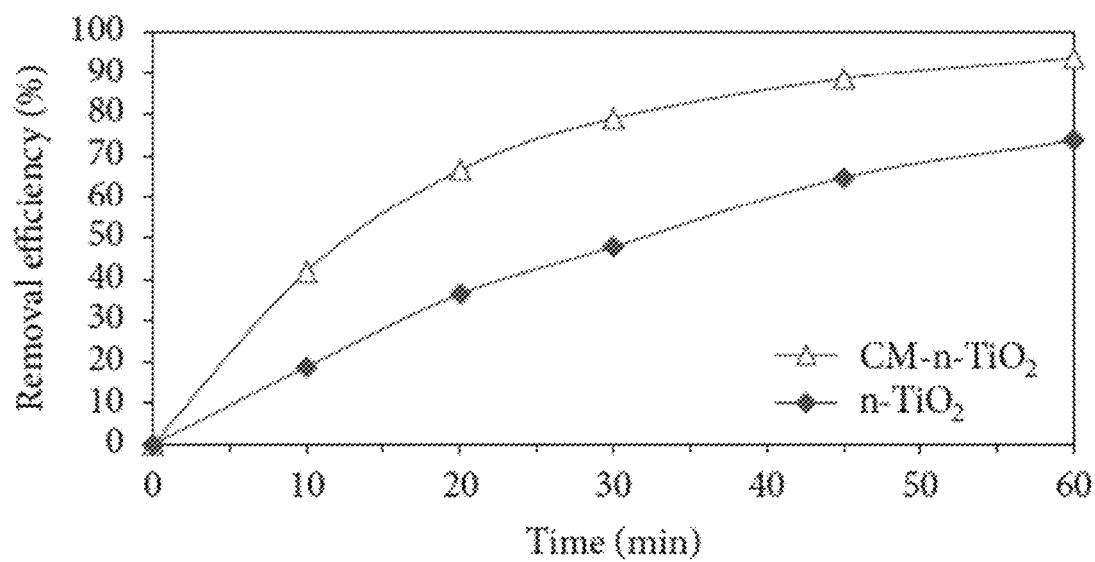
FIG. 21 is a comparative plot of photocatalytic degradation of a mixture of Ar 1254 (0.5 ppm) and Ar 1260 (0.5 ppm) in seawater at pH 5 under illumination of natural sunlight at pilot plant scale using an unmodified titanium dioxide nanoparticle (n-$TiO_2$) photocatalyst dosage of 0.5 g $L^{-1}$ compared to a carbon-modified titanium dioxide nanoparticle (CM-n-$TiO_2$) photocatalyst dosage of 0.5 g $L^{-1}$.

In contrast, a comparison with regular $n$-$TiO_2$ was performed under the same experimental conditions in order to assess the photocatalytic performance of $CM$-$n$-$TiO_2$ in the SFFR for the degradation of Ar 1254 (0.5 ppm), Ar 1260 (0.5 ppm), and a mixture of Ar 1254 (0.5 ppm) and Ar 1260 (0.5 ppm). FIG. 19, FIG. 20, and FIG. 21 shows the photocatalytic degradation of Ar 1254 (0.5 ppm) (FIG. 19), Ar 1260 (0.5 ppm) (FIG. 20), and a mixture of Ar 1254 (0.5 ppm) and Ar 1260 (0.5 ppm) (FIG. 21) in seawater at advantageous conditions of pH 5 and 0.5 g $L^{-1}$ of the photocatalysts $n$-$TiO_2$ and $CM$-$n$-$TiO_2$, respectively. As a result of carbon incorporation, a remarkably higher photodegradation efficiency of $CM$-$n$-$TiO_2$ is clear, reflecting the capability of $CM$-$n$-$TiO_2$ to harvest maximum solar light photons and hence enhance the degradation efficiency. After 60 minutes of solar irradiation, PCBs were easily degraded with efficiencies of 92.1% for Ar 1254 (FIG. 19), 94.6% for Ar 1260 (FIG. 20), and 93.7% for the mixture of Ar 1254 and Ar 1260 (FIG. 21).

Example 11

Kinetic Studies of Photocatalytic Removal Experiments in Seawater at Pilot-Plant Scale To depict the kinetics of photocatalytic reactions of aqueous seawater organics the Langmuir-Hinshelwood (L-H) model was employed. According to this model, the relationship between the relationship between the degradation rate (r) and concentration of the reactant in water at time t(C), can be expressed by formula (VIII).

$$r = -\frac{dc}{dt} = \frac{k_r K_{ad}}{1 + K_{ad}C} \quad (VIII)$$

In this formula, the constants $k_r$ and $K_{ad}$ represent the rate and the adsorption equilibrium. This equation can be simplified to represent the pseudo-first order reaction when $C_0$ is very small by formula (IX).

$$\ln\left(\frac{C_0}{C}\right) = k_r k_{ad} t = k_{app} t \quad (IX)$$

In this formula, $k_{app}$ and $C_0$ are the apparent first-order rate constant and the concentration at zero time, respectively. The half-life time reaction ($t_{1/2}$), the amount of time required for 50% of the initial concentration to disappear, can be calculated by formula X.

$$t_{1/2} = \frac{\ln(2)}{k_{app}} \quad (X)$$

Figure 22:
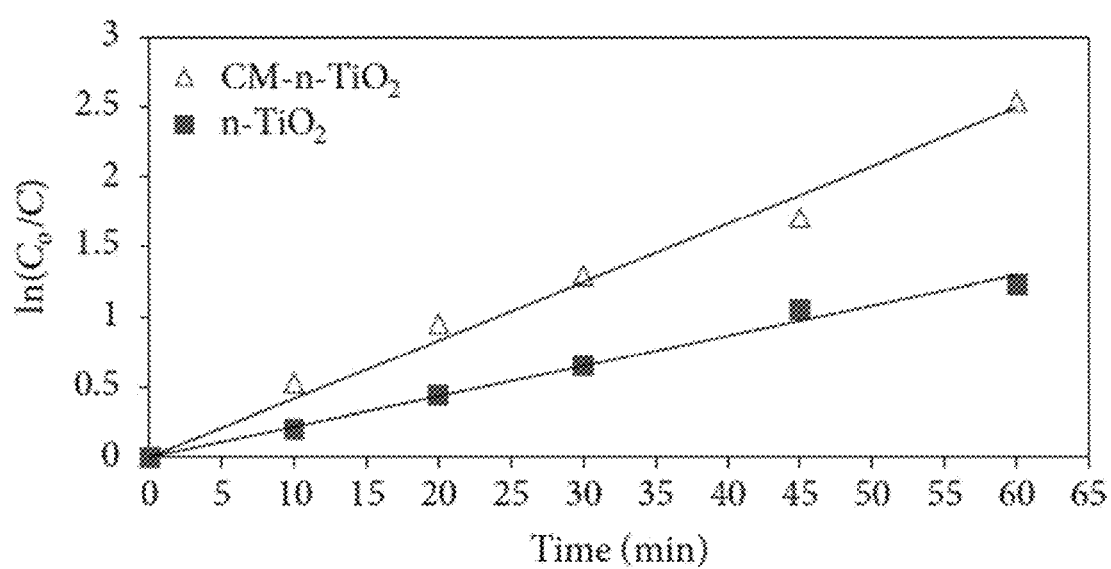
FIG. 22 is a kinetic analysis plot of the photocatalytic degradation of 0.5 ppm Aroclor 1254 (Ar 1254) in seawater under illumination of natural sunlight at pilot plant scale using an unmodified titanium dioxide nanoparticle (n-TiO$_2$) photocatalyst compared to a carbon-modified titanium dioxide nanoparticle (CM-n-TiO$_2$) photocatalyst.
Figure 23:
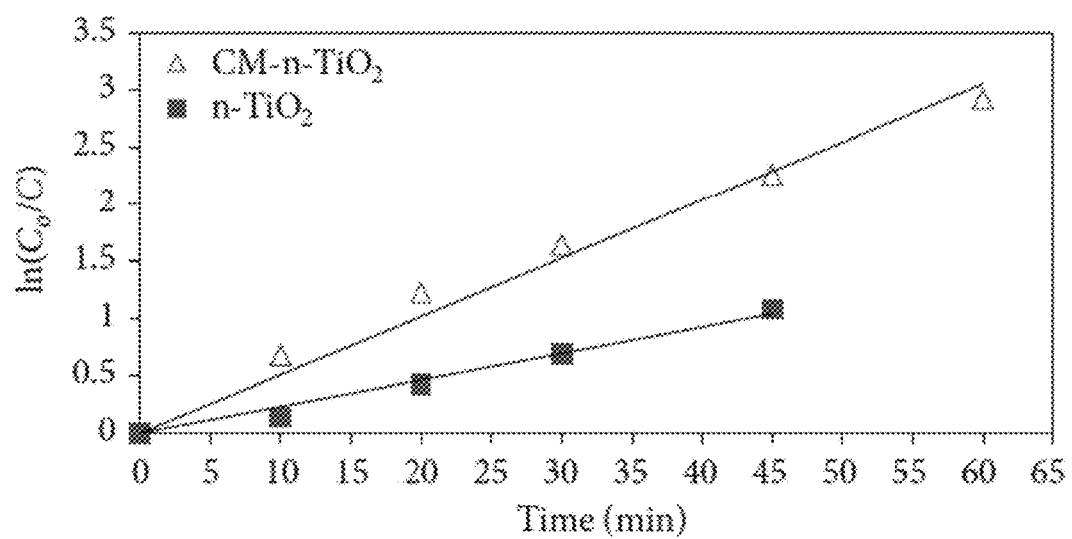
FIG. 23 is a kinetic analysis plot of the photocatalytic degradation of 0.5 ppm Aroclor 1260 (Ar 1260) in seawater under illumination of natural sunlight at pilot plant scale using an unmodified titanium dioxide nanoparticle (n-TiO$_2$) photocatalyst compared to a carbon-modified titanium dioxide nanoparticle (CM-n-TiO$_2$) photocatalyst.
Figure 24:
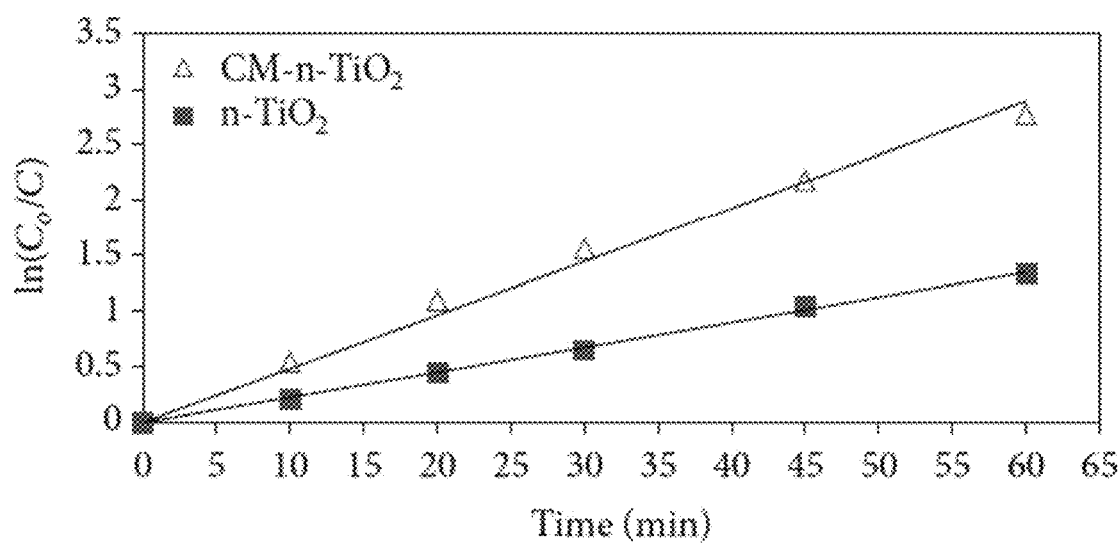
FIG. 24 is a kinetic analysis plot of the photocatalytic degradation a mixture of Ar 1254 (0.5 ppm) and Ar 1260 (0.5 ppm) in seawater under illumination of natural sunlight at pilot plant scale using an unmodified titanium dioxide nanoparticle (n-TiO$_2$) photocatalyst compared to a carbon-modified titanium dioxide nanoparticle (CM-n-TiO$_2$) photocatalyst.

By plotting ln ($C_0$/C) versus irradiation time (t) a linear behavior that indicates a pseudo-first order kinetics for the photocatalytic degradation of PCBs was obtained. FIG. 22, FIG. 23, and FIG. 24 shows these plots for photocatalytic degradation of Ar 1254 (0.5 ppm) (FIG. 22), Ar 1260 (0.5 ppm) (FIG. 23), and a mixture of Ar 1254 (0.5 ppm) and Ar 1260 (0.5 ppm) (FIG. 24), respectively. From the apparent rate constant, calculated from the slope of the linear plot, and $t_{1/2}$ values, it is interesting to note that the solar photocatalytic degradation of PCBs using the pilot plant (SFFR) in the presence of CM-n-TiO$_2$ is twofold faster in comparison with that of regular unmodified TiO$_2$, confirming the potentiality of the CM-n-TiO$_2$/SFFR as an efficient system for the photocatalytic degradation of water. Table 2 summarizes the kinetic parameters of each catalyst.

TABLE 2

Kinetic parameters of CM-n-TiO$_2$ and n-TiO$_2$ nanoparticles in seawater at pilot-plant scale (SFFR)

| PCBs | CM-n-TiO$_2$ | | | n-TiO$_2$ | | |
| --- | --- | --- | --- | --- | --- | --- |
| | $k_{app}$ (min$^{-1}$) | $t_{1/2}$ (min) | $R^2$ | $k_{app}$ (min$^{-1}$) | $t_{1/2}$ (min) | $R^2$ |
| Ar 1254 (0.5 ppm) | 0.0416 | 16.66 | 0.9854 | 0.0218 | 31.80 | 0.9759 |
| Ar 1260 (0.5 ppm) | 0.0509 | 13.62 | 0.9818 | 0.0231 | 30.01 | 0.985 |
| Ar 1254 (0.5 ppm) + Ar 1260 (0.5 ppm) | 0.0482 | 14.38 | 0.9909 | 0.0225 | 30.81 | 0.9983 |

In conclusion, unique carbon-modified titanium oxide (CM-n-TiO$_2$) nanoparticles were successfully fabricated via a sonicated sol-gel method using titanium (IV) isopropoxide as a Ti and a carbon-containing precursor. Comparative evaluation of the photocatalytic performance of carbon-modified and regular unmodified titanium oxide toward the photocatalytic removal of PCBs was performed in aqueous solution at lab scale, in seawater at lab scale, and in seawater at pilot-plant scale confirming that CM-n-TiO$_2$ is a highly active photocatalyst. The bandgap energy has been reduced from 2.99 eV for n-TiO$_2$ to 1.8 eV for CM-n-TiO$_2$, which in turn improved the photocatalytic performance of CM-n-TiO$_2$ by absorption of more light photons. The results showed that the removal rate of PCBs was favorable at catalyst dosage of 0.5 g L$^{-1}$ and pH 5. The photodegradation kinetics of PCBs using CM-n-TiO$_2$ followed a pseudo-first order reaction. The photocatalytic degradation of PCBs in seawater has been successfully achieved using CM-n-TiO$_2$ nanoparticles at laboratory level with UV light and at pilot-plant scale (SFFR) under natural solar radiation. Furthermore, the results obtained evidenced the validity of the CM-n-TiO$_2$/SFFR system as an attractive and promising technique for the remediation of polluted water.

Thus, the foregoing discussion discloses and describes merely exemplary embodiments of the present disclosure. As will be understood to those skilled in the art, the present disclosure may be embodied in other specific forms without departing from the spirit or essential characteristics thereof. Accordingly, the disclosure of the present invention is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A closed-loop system for remediation of an aqueous solution comprising a polychlorinated biphenyl, the system comprising:
   a vessel comprising an aqueous solution comprising a first amount of at least one polychlorinated biphenyl and carbon modified titanium dioxide nanoparticles having a Ti:C atomic ratio in the range of 3:1 to 6:1 and a bandgap in the range of 1.4-1.8 eV dispersed in the aqueous solution;
   a pump;
   a tray oriented at a tilt angle from the horizontal comprising a distributor end and an opposing collector end located at a lower vertical height than the distributor end; and wherein the vessel is configured to deliver the aqueous solution through the pump to the distributor end of the tray;

wherein the tray is configured to flow the aqueous solution along the tray via entirely gravity from the distributor end to the collector end while exposing the aqueous solution to a light source thereby forming a remediated aqueous solution comprising a second amount of the at least one polychlorinated biphenyl;

wherein the collector end is configured to return the remediated aqueous solution to the vessel; and wherein the first amount of the at least one polychlorinated biphenyl is greater than the second amount of the at least one polychlorinated biphenyl.

2. The system of claim 1, wherein the carbon modified titanium dioxide nanoparticles have a 5-10% atomic percentage of carbon relative to the total atomic percentage of the carbon modified titanium dioxide nanoparticles.

3. The system of claim 1, wherein the carbon modified titanium dioxide nanoparticles have an average crystal size of 25-35 nm.

4. The system of claim 1, wherein the tray is oriented at a tilt angle of 5-40° from the horizontal.

5. The system of claim 1, wherein the light source is the sun.

6. The system of claim 1, wherein the carbon modified titanium dioxide nanoparticles have a bandgap in the range of 1.78-1.8 eV.

7. The system of claim 1, wherein the carbon modified titanium dioxide nanoparticles contain predominantly titanium dioxide in an anatase phase.

8. The system of claim 1, wherein the carbon modified titanium dioxide nanoparticles comprise carbon in the form of a carbide.

9. A method for remediating an aqueous solution comprising at least one polychlorinated biphenyl employing the system of claim 1, the method comprising:

flowing the aqueous solution from the vessel to the distributor end of the tray;

flowing the aqueous solution from the distributor end of the tray to the collector end of the tray via gravity while exposing the aqueous solution to the light source thereby photocatalytically degrading or mineralizing the at least one polychlorinated biphenyl to obtain the remediated aqueous solution; and returning the remediated aqueous solution to the vessel.

10. The method of claim 9, wherein greater than 70% by weight of the polychlorinated biphenyl relative to the first amount of the at least one polychlorinated biphenyl is photocatalytically degraded or mineralized after the exposing is carried out for a time period of 10-60 minutes.

11. The method of claim 9, wherein the aqueous solution, the remediated aqueous solution, or both continuously circulates in a closed-loop circuit.

12. The method of claim 9, wherein greater than 90% by weight of the polychlorinated biphenyl relative to the first amount of the at least one polychlorinated biphenyl is phototcatalytically degraded or mineralized after the exposing is carried out for a time period of less than 60 minutes.

13. A photocatalyst, comprising:

carbon modified titanium dioxide nanoparticles which have a Ti:C atomic ratio in the range of 3:1 to 6:1;

wherein the photocatalyst has a bandgap in the range of 1.4-1.8 eV.

14. The photocatalyst of claim 13, which has a 5-10% atomic percentage of carbon relative to the total atomic percentage of the photocatalyst.

15. The photocatalyst of claim 13, wherein the carbon modified titanium dioxide nanoparticles have an average crystal size of 25-35 nm.

16. The photocatalyst of claim 13, wherein the carbon modified titanium dioxide nanoparticles have a bandgap in the range of 1.78-1.8 eV.

17. The photocatalyst of claim 13, wherein the carbon modified titanium dioxide nanoparticles contain predominantly titanium dioxide in an anatase phase.

18. The photocatalyst of claim 13, wherein the carbon modified titanium dioxide nanoparticles comprise carbon in the form of a carbide.

* * * * *